United States Patent [19]

Vanin et al.

[11] Patent Number: 5,710,037
[45] Date of Patent: Jan. 20, 1998

[54] RETROVIRAL VECTOR PARTICLES

[75] Inventors: Elio F. Vanin; Arthur W. Nienhuis, both of Memphis, Tenn.

[73] Assignee: The United States of America as represented by the Department of Health and Human Services, Washington, D.C.

[21] Appl. No.: 258,420

[22] Filed: Jun. 10, 1994

[51] Int. Cl.$^6$ .......................... C12N 15/86; C12N 15/63; C12N 15/48; C12N 5/10

[52] U.S. Cl. .................. 435/240.2; 424/93.2; 424/93.21; 435/240.1; 435/320.1; 536/23.72; 536/24.1

[58] Field of Search ........................... 435/320.1, 240.1, 435/240.2; 536/23.72, 24.1; 424/93.2, 93.21

[56] References Cited

PUBLICATIONS

Van Beveren et al., J. Virol. 41(2):542–556 (1982).
O'Neill et al., J. Virol. 53(1):100–106 (1985).
Adachi, et al., J. Virol., vol. 50, No. 3, pp. 813–821 (Jun. 1984).
Ott, et al., J. Virol., vol. 64, No. 2, pp. 757–766 (Feb. 1990).
Donahue, et al., J. Exp. Med., vol. 176, pp. 1125–1135 (Oct. 1992).

Primary Examiner—Mindy Fleisher
Assistant Examiner—Johnny F. Railey, II
Attorney, Agent, or Firm—Elliot M. Olstein; Raymond J. Lillie

[57] ABSTRACT

A retroviral vector which includes a nucleic acid sequence encoding a retroviral envelope. The nucleic acid sequence encoding a retroviral envelope includes a first nucleic acid sequence encoding a first envelope portion which is a portion of MCF viral gp 70 protein, a nucleic acid sequence which encodes xenotropic envelope, a nucleic acid sequence which encodes an amphotropic envelope portion, and a nucleic acid sequence which encodes p15E protein. Such retroviral envelopes encoded by such nucleic acid sequence may be included in infectious viral particles. The infectious viral particles also may include gene(s) encoding therapeutic agents, and thus may be used in gene therapy.

18 Claims, 44 Drawing Sheets

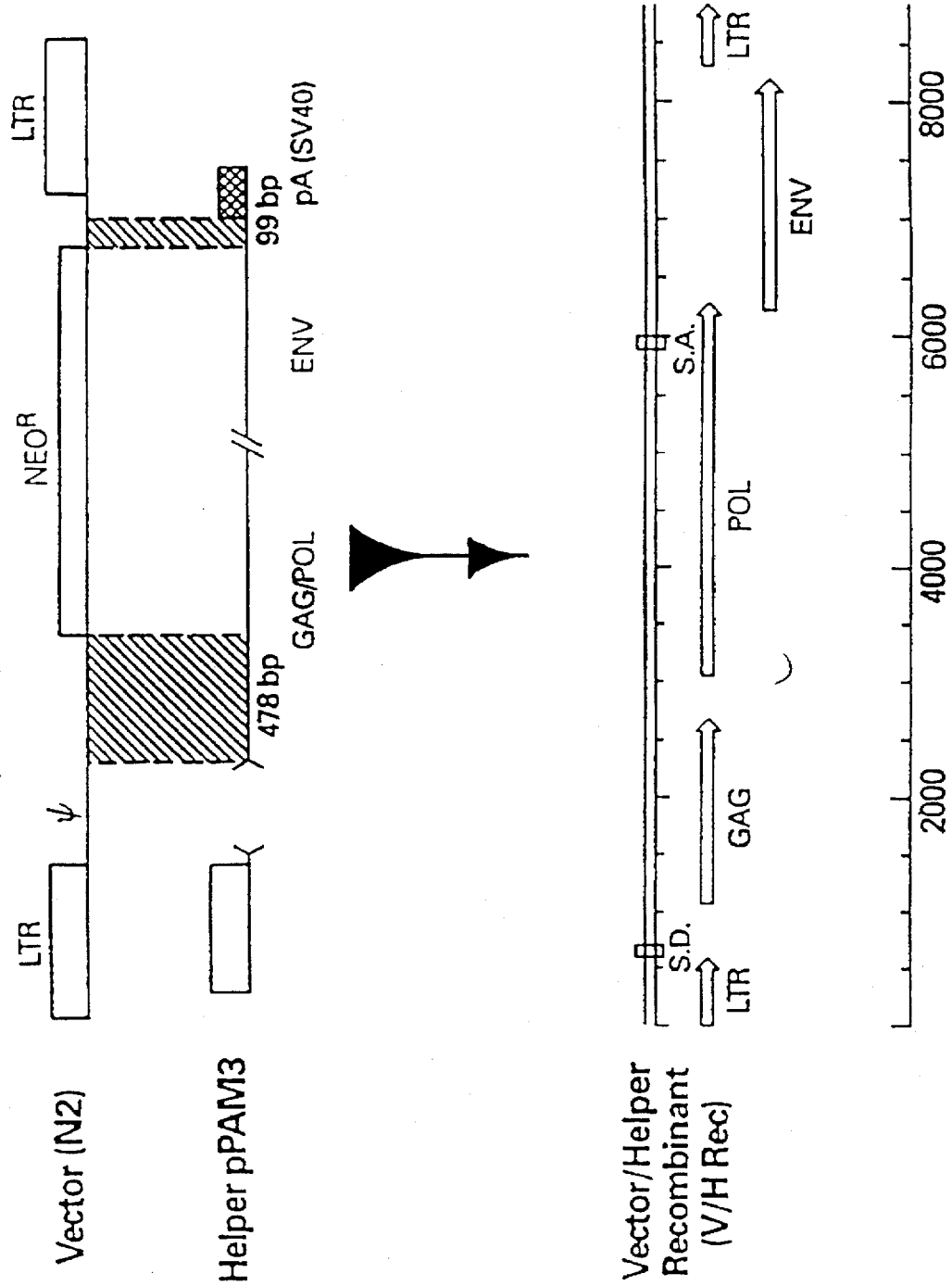

| | |
|---|---|
| FIG. 5Aa | FIG. 5Ab |
| FIG. 5Ac | FIG. 5Ad |
| FIG. 5Ae | FIG. 5Af |
| FIG. 5Ag | FIG. 5Ah |
| FIG. 5Ai | FIG. 5Aj |

MATCH WITH FIG. 5Ab

```
MCF FrNx    ATGGAAGGTCCAGCGTTCTCAAAACCCCTTAAAGATAAGATTAACCCGTGG
Clone 24    ATGGAAGGTCCAGCGTTCTCAAAACCCCTTAAAGATAAGATTAACCCGTGG
V/H         ATGGCGCGTTCAACGCTCTCAAAACCCCTCAAGATAAGATTAACCCGTGG
                                                         .150

TGACAGCCCTCACCAAGTCTCTTCAATGTTACTTGGAGAGTTACCAACTTAATGAGAGGACAAA
            TGACAGCCCTCACCAAGTCTCTTCAATGTTACTTGGAGAGTTACCAACTTAATGAGAGGACAAA
            --AGAGCCCCATCAGGTCTCTTTAATGTAACCTGGAGAGTCACCAACCTGATGACTGGGCGTA

TACTTCGACTTGTGCGATTTAATAGGGGACGATTGGGA----TGAGACC-GGAC-------T
            TACTTCGACTTGTGCGATTTAATAGGGGACGATTGGGA----TGAGACT-GGAC-------T
            TATTTTGATCTATGTGATCTGGTCGGAGACGAGTGGGACCCTTCAGACCAGGAACCGTATGT
                                        .250

.350

TCTATGTTTGCCCCGGGCATACTGTACCAACAGGTGTGGAGGGCCGAGAGAGGGCTACTGT
            TCTATGTTTGCCCCGGGCATACTGTACCAACAGGTGTGGAGGGCCGAGAGAGGGCTACTGT
            TCTATGTTTGCCCCGGGCATACTGTACCAACAGGGTGTGGAGGGCCGAGAGAGGGCTACTGT
                        MATCH WITH FIG. 5Ac
```

FIG. 5Ab

```
                                                        .100
GGCCCCCTGATAGTCCTGGGGATCTTAATAAGGGCAGGAGTATCAGTACAACA
GGCCCCCTGATAGTCCTGGGGATCTTAATAAGGGCAGGAGTATCAGTACAACA
   AAGCCCTTAATAGTCATGGGAGTCCTGTTAGGAGTAGGGATGGCAG------

.200
CAGCTAACGCTACCTCCCCTGGGACAATGACAGATGCCTTTCCTATGCTG
CAGCTAACGCTACCTCCCCTGGGACAATGACAGATGCCTTTCCTATGCTG
CCGCCAATGCCACCTCCCCTGGGAACTGTACAAGATGCCTTCCCAAAATTA

.300
TGGGTGTCGCA------CTCCCGGGGAAGAAAAAGGGCAAGAACATTTGACT
TGGGTGTCGCA------CTCCCGGGGAAGAAAAACGGGCAAGAACATTTGACT
CGGGTATGGCTGCAAGTACCCCGCAGGGAGACAGCCGGGACTTTTGACT

.400
GGCAAATGGGGCTGTGAGACCACTGACAGGCATACTGGAAGCCATCATCATC
GGCAAATGGGGCTGTGAGACCACTGACAGGCATACTGGAAGCCATCATCATC
GGCAAATGGGGCTGTGAGACCACTGACAGGCATACTGGAAGTCATCATCATC
```

MATCH WITH FIG. 5Ad

MATCH WITH FIG. 5Aa

FIG. 5Ac

MATCH WITH FIG. 5Ad

```
Match with FIG.5Aa                                                                                        .700
         TTTACGTGTGCCCTGGGCATACCGTAAAGTCGGGGTGTGGGGACCAGGAGAGGCTACTGT
         ||||||||||||||||||||||||||||||||||||||||||||||||||||||||||||
         ATGGGACCTAATTTCCCTTAAGCGAGGAAACACCCCTCGGAATCAGGG------------
         ||||||||||||||||||||||||||||||||||||||||||||||||
         ATGGGACCTAATTTCCCTTAAGCGAGGAAACACCCCTCGGAATCAGGG------------
         ||||||||||||||||||||||||||||||||||||||||||||||||
         GTGGGACCTAATCTCCCTTAAGCGGGTAACACCCCTGGGACACGGGATGCTCTAAAGTTG
                       .450                                  .550
         ACACCGGGGGGTCGATGCAATCCCCTAGTCCTAGAATTCACTGACGCGGGTAAAAAGGCCAG
         ||||||||||||||||||||||||||||||||||||||||||||||||||||||||||||
         ACACCGGGGGGTCGATGCAATCCCCTAGTCCTAGAATTCACTGACGCGGGTAAAAAGGCCAG
         ||||||||||||||||||||||||||||||||||||||||||||||||||||||||||||
         ACTCGAGGGGCAGATGCAACCCTCTAGTCCTAGAATTCACTGATGCAGGAAAAAAGGCTAA
                                          .650
         ACCCGGTGACCCGGTTCTCTTTGACCCGCCAGTCCTCAATATAGGGCCCCGCATCCCCATT
         ||||||||||||||||||||||||||||||||||||||||||||||||||||||||||||
         ACCCGGTGACCCGGTTCTCTTTGACCCGCCAGTCCTCAATATAGGGCCCCGCATCCCCATT
         ||||||||||||||||||||||||||||||||||||||||||||||||||||||||||||
         ATCCTATTACCATGTTCTCCCTGACCCGGCAGGCTTCTAAGTGTGGGACCCCGAGTCCCCATA
```

MATCH WITH FIG. 5Ae

FIG. 5Ad

MATCH WITH FIG. 5Ab

```
GGTAAATGGGGGTGTGAAACCACCGGACAGGCTTACTGGAAGCCCACATCATC

------CCCCTGTGTTATGATTCCTCAGTGGTCTCCAGTGGCATCCAAGGTGCC
------GGCCTGTGTTATGATTCCTCAGTGGTCTCCAGTGGCATCCAGGGTGCC
       CCTGTGGCCCCTGCTACGACCTCTCCAAAGTATCCAATTCCTTCCAAGGGCT
                                 .500
       CTGGGATGGCCCCAAAGTATGGGACTAAGACTGTACCGATCCACAGGATCG
       CTGGGATGGCCCAAAGTATGGGACTAAGACTGTACCAATCCACAGGATCG
       CTGGGACGGCCCAAAGTATGGGACTAAGACTGTACCAATCCACAGGATCG
                                 .600
       GGGCCTAATCCCGTGATCACTGGCCAACTACCCCCCGACCCCGTGCAGAT
       GGGCCTAAT CCCGTGATCACTGGCCAACTACCCCCCGACCCCGTGCAGAT
       GGGCCCAAC CCAGTATTACCCGACCAAAGACTCCCTTCCTCACCAATAGAGAT
                                 .750
```

MATCH WITH FIG. 5Af

MATCH WITH FIG. 5Ac

FIG. 5Ae

MATCH WITH FIG. 5Af

MATCH WITH FIG. 5Ac

MATCH WITH FIG. 5Ag

```
                                                                           CTACAGG
----CAGGCTCCCCAGGCCTCCTCAGCCTCCTC-------------------------                 CTACAGG
----CAGGCTCCCCAGGCCTCCTCCTCAGACTCCTC-----------------------                CTACAGG
TGTACCGGCTCCACAGCCACCT--AGCCCCCCTCAATATACCAGTTACCCCCCTTCCACTACCAG
                                      .900
GGACGGGAGACAGGCTGCTAAACCTGGTAGATAGAGCATACCAAGCACTCAACCTCACCAGT
GGACGGGAGACAGGCTGCTAAACCTGGTAGATGGAGCATACCAAGCACTCAACCTCACCAGT
GAACTGGAGATAGACTACTAGCTCTAGTCAAAGGAGCCTATCAGGCGCTTAACCTCACCAAT
                                      .1000
CGAAGGGGTTGCCGTCCTAGGTACTTACTCCAACCATACCCTCTGCCCCAGCTAAACTGCTCCG
CGAAGGGGTTGCCGTCCTAGGTACTTACTCCAACCATACCCTCTGCCCCAGCTAAACTGCTCCG
CGAAGGAGTAGCGGTCGTGGGCACTTATACCAATCATTCCACCGCTCCGGCCAACTGTACGG
                                      .1100
ATAGGAACAGTCCCAAAAACTCACCAGGCCCTGTGCAACACTACCCTTAAGGCAGGCAAAGG
GTAGGAGCAGTTCCCAAAACCCATCAGGCCCTGTAATACCACCCAAAAGACGAGCGACGG
ATGGGAGCAGTACCTAAAACTCACCAGGCTTTATGTAACACCACCCAAAGCGCCGGCTCAGG
```

FIG. 5Af

MATCH WITH FIG. 5Ad

```
        .800                                                                                                                                        
CGCAGCCTC TATGGTCCCT------GGGACTGCCCCACCTTCTCAACAACCTG
|||||||||  |||||||||||      ||||||||||||  |||||||||||
CGCAGCCTC TATGGTCCCT------GGGACTGCCCCACCGTCTCAACAACCTG

TACACCCCTC AACCTCCCCTACAAGTCCCCTACAAGTCCAAGTGTCCCACAG----CTACCCCCAG
                                                           .950

CCTGACAAA ACCCAAGAGAGTGCTGGTTGTGTCTGGTATCGGGACCCCCCTACTA
||||||||| |||||||||||||||||||||||||||||||||||||||||||||
CCTGACAAA ACCCAAGAGAGTGCTGGTTGTGTCTGGTATCGGGACCCCCCTACTA
|||||||   |||||||||||||||||||||||||||||||||||||||||||||
CCCGACAAG ACCCAAGAATGTTGGCTGTGCTTAGTGTCGGGACCTCCTTATTA
                                                1050

TGGCCTCCC AACACAAGCTGACCCTGTCCGAAGTGACTGGACGGGACTCTGC
|||||||||  |||||||||||||||||||||||||||||||||||||||
CGGCCTCCC AACACAAGCTGACCCTGTCCGAAGTAACCGGACACAGGACTCTGC
|| ||||||  ||||||| ||||||||||||||||||   | | ||||||
CCACTTCCC AACATAAGCTTACCCTATTTGAAGTGACAGGACCAGGCCTATGC
                                                  .1150

GTCTTACTA TCTAGTTGCCCCCACAGGAACTATGTGGCATGTAACACTGGAC
|||||||||  ||||||| |||||| ||| |||||||| |||||||||||||
GTCCTACTA TCTGGCTGCTCCCCGCCGGGACCATTGGGCTTGCAACACCGGGC
||| |||||  || ||| | ||  ||||||||||||||||| |||| ||||
ATCCTACTA CCTTGCAGCACCCGCCGGAACAATGTGGGCTTGCAGTACTGGAT
```

MATCH WITH FIG. 5Ah

MATCH WITH FIG. 5Ae

FIG. 5Ag

Match with FIG.5Ah

MATCH WITH FIG.5Ae

```
                    .1200
TCACTCCATGCCTATCTGCCACCGTGCTTAATCGCACCACTGACTATGGCGTTCTCGTGGAA
|||||||||||||||||| |||||||||||||||||  ||||| |||| |||||| |||||
TCACTCCCTGCCTATCTACTACTGTGCTTAATCTAACTACTCAATCTAACCATAGATTATTGTGTATTAGTTGAA
                                  |||||||||||||||| ||||||||||
                              TGACTCCCTGCTTGTCCACCACGGTGCTCAATCTAACCACAGATTATTGTGTATTAGTTGAA

.1300                                          .1350
AAAATCCTATAGACACATAAAAGAGAACTAGTGTCCTTAACCTTGGCCTTAGTATTAGGTGGGC
||||||||||||| |||||||||||||||||||||||||||||||||||||||||||||||||
ACAGCGTACCAAATATAAAAGAGAGCCAGTAGCATTGACCCTGGCCCTTCTAGTAGGAGGAT
||||||||||||||||||||||||||||||||||||||||||||||||||||||||||||
ACAGCGTACCAAATATAAAAGAGAGCCAGTAGCCAGTATCATTGACCCTGGCCCTTCTACTAGGAGGAT

.1450
GCCACCTAGCAGTTTGAGCAGCTCCATGCTGCCGTACAAGATGATCTCAAAGAAGTAGAAAA
|||||||||||||||||||||||||||||||||||||||||||||||||||||||||||||
AAAACCCAGCAGTTTGAGCAGCTTCATGCCGCTATCCAGACAGACCTCAACGAAGTAGAAAA
||||||||||||||||||||||||||||||||||||||||||||||||||||||||||||
AAAACCCAGCAGTTTGAGCAGCTTCATGCCGCTATCCGCAGACAGACCTCAACGAAGTCGAAAA

.1550
AGAATCGACGAGGCCTAGACCTGTGTTCCTAAAAAGAGGAGGACTGTGTGCTGCCCTAAAA
|||||||||||||||||||||||||||||||||||||||||||||||||||||||||||
AGAACCGCAGAGGCCTAGATTTGCTATTCCTAAAAGGAGGAGGTCCTCCGGCCAGCCCTAAAA
||||||||||||||||||||||||||||||||||||||||||||||||||||||||||||
AGAACCGCAGAGGCCTAGATTTGCTATTCCTAAAGGAGGAGGGAGGTCTCTGCGCAGCCCTAAAA
```

MATCH WITH FIG.5Ai

FIG. 5Ah

MATCH WITH FIG.5Af

```
.1250
TTATGGCCCAGGGTCACCTACTATCCTTCCAGTTACGTCTATAGCCAGTTTGA
||||||||||  |||||||||||||| |||||||||||||  |||||||||||
CTCTGGCCCAGAGTAATTTACCACTCCCCCGATTATATGTATGGTCAGCTTGA
||||||||||||||||||||||||||||||||||||||||||||||||||||
CTCTGGCCCAGAGTAATTTACCACTCCCCCGATTATATGTATGGTCAGCTTGA

.1400
TAACTATGGGTGGCATTGCCGCGGGAGTAGGGATAGGAACTACCCGCCCTGGCC
|||| ||||| ||||||||  ||||||||||||||||||||||||||| ||||
TAACCATGGGAGGGATTGCAGCTGGAATAGGGACGGGGACCACTGCCTTAATT
|||||||||||||||||||||||||||||||||||||||||||||||||||||
TAACCATGGGAGGGATTGCAGCTGGAATAGGGACGGGGACCACTGCCTTAATT

.1500
GTCAATTACTAACCTAGAAAAAGTCTCTTACTTCGTTGTCGGAGGTTGTACTGC
||||||||| ||||||||||||||| |||||||||||||||||||||||| ||
GTCAATTACCAACCTAGAAAAAGTCACTGACCTCGTTGTCTGAAGTAGTCCTAC
|||||||||||||||||||||||||  |  ||||||||||||||||||||||||
GTCAATTACCAACCTAGAAAAAGTCATTGACCTCGTTGTCTGAAGTAGTCCTAC

.1600
GAAGAATGTTGTTCTATGCTGACTATACAGGCCTAGTAAGAGAGATAGTATGGC
|||||||||||||| |||||||  ||||||||| ||||||||||||| |||||
GAAGAATGTTGTTTTTATGCAGACCACACGGGGCTAGTGAGACAGCAGCATGGC
|||||||||||||||||||||||||||||||||||||||||||||||||||||
GAAGAATGTTGTTTTTATGCAGACCACACGGGGCTAGTGAGACAGCAGCATGGC
                   MATCH WITH FIG.5Aj
```

MATCH WITH FIG. 5Ag

FIG. 5Ai

MATCH WITH FIG. 5Ag

MATCH WITH FIG. 5Aj

```
         .1650                                    .1700
CAAATTAAGAGAGAGACTCTCTCAGAGACAAAAACTATTTGAGTCGAGCCAAGGATGGTTCG    MCF FrNx
||||||||||||||||||||||||||||||||||||||||||||||||||||||||||||    
CAAATTAAGAGAGAGACTCTCTCAGAGACAAAAACTATTTGAGACAGGCCAAGGATGGTTCG    Clone 24
||||||||||||||||||||||||||||  ||||||||||||||||||||||||||||||    
CAAATTAAGAAAAGGCTTAATCAGAGACAAAAACTATTTGAGACAGGCCAAGGATGGTTCG    V/H .1800
GGGCCTTCTATTATACTCCTACTAATTCTGCTTTTTGGACCCTGCATTCTTAATCGATTAGT   MCF FrNx
||  |||||| ||||| ||||||| ||||| ||||||||||||||||||||||||||||||
GGACCTCTAATAGTACTCTTACTGATCTCTTGGACCTTGCATTCTTAATCGATTAGT   Clone 24
||||||||||||||||||||||||||||||||||||||||||||||||||||||||||||
GGACCTCTAATAGTACTCTTACTGATCTCTTGGACCTTGCATTCTTAATCGATTAGT   V/H .1900
AATACCACCAGCTAAAACCACTAGAATACGAGCCACAATAA         MCF FrNx
|||| ||||||||||||||||||||| |||||||||||   ---TAG
AATATCACCAGCTGAAGCTTATAGAGTACGAGCCA---TAG   Clone 24
|||||||||||||||||||||||||||||||||||   ---TAG
AATATCACCAGCTGAAGCTTATAGAGTACGAGCCA---TAG   V/H
```

FIG. 5AJ

MATCH WITH FIG. 5Ah

```
AAGGATGGTTTAACAGATCCCCCTGGTTTACCACGTTGATATCCACCATCATG
           |||||||| |||||||||||||| ||||||||| ||||||||||||||
AAGGGCTGTTTAATAGATCCCCCTGGTTTACCACCTTAATCTCCACCATCATG
|||||||||||||||||||||||||||||||||| ||||||||||||||||||
AAGGGCTGTTTAATAGATCCCCCTGGTTTACCACCTTAATCTCCACCATCATG
                                                      .1750

TCAATTTGCTAAAAGACAGGATCTCAGTAGTCCAGGCTTTAGTCCTGACTCAAC
 |||||||||||||||||||||| |||||||||||||||| |||||||||||||
CCAATTTGTTAAAGACAGGATATCAGTGGTCCAGGCTCTAGTTTTGACTCAAC
||||||||| |||||||||||||||||||||||||||||||||||||||||||
CCAATTTGT.TAAAGACAGGATATCAGTGGTCCAGGCTCTAGTTTTGACTCAAC
                     .1850
```

MATCH WITH FIG. 5Ai

FIG. 5Ca

```
GAAAGACCCCCACCCTGTAGGTTTGGCAAGCTAGCTTAAGTAACGCCATTTGCAAGGCA
     ----+----:----+----:----+----:----+----:----+----:----+----:
TGGAAAAATACATAACTGAGAATAGAGAAGTTCAGATCAAGG
100
CTTCTGGGGTGGACATCCAAACCGTTCGATCGAATTCATTGCGGTAAAACGTTCCGTA
CCTTTTTATGTATTGACTCTTATCTCTCTTCAAGTCTAGTCC
TCAGGAACAGATGGAACAGCTGAATATGGGCCAAACAGGATATCTGTGGTAAGCAGTT
CCTGCCCCGGCTCAGAAGCAGTTCCTGCCCCGGCTCAGGGCC
     ----+----:----+----:----+----:----+----:----+----:----+----:
200
AGTCCTTGTCTCTACCTTGTGTCGACTTATACCCGGTTTGTCCTATAGACACCATTCGTCAAG
GACGGGGCCGAGTCTTCGTCAAGGACGGGGCCGAGTCCCGG
AAGAACAGATGGAACAGCTGAATATGGGCCAAACAGGATATCTGTGGTAAGCAGTTCC
TGCCCCGGCTCAGGGCCAAGAACAGATGGTCCCCAGATGCGG
```

MATCH WITH FIG. 5Cb

FIG. 5Cb

MATCH WITH FIG. 5Ca

300 TTCTTGTCTACCTTGTCGACTTATACCCGGTTGTCCTATAGACACCATTCGTCAAGGA

CGGGGCCGAGTCCCGGTTCTGTCTACCAGGGGTCTACGCC

TCCAGCCCTCAGCAGTTTCTAGAGAACCATCAGATGTTCCAGGGTGCCCAAGGACCT

GAAATGACCCTGTGCCTTATTGAACTAACCAATCAGTTCG

400 AGGTCGGGAGTCGTCAAAGATCTCTTGGTAGTCTACAAAGGTCCCACGGGGTTCCTGG

ACTTTACTGGGACACGGAATAAACTTGATTGGTTAGTCAAGC

CTTCTCGCTTCTGTTCGGGCCTTCGCTCCCCGAGCTCAATAAAAAAGCCCACAACCC

CTCACTCGGGGCGCCAGTCCTCCGATTGACTGAGTCGCCCG

500

MATCH WITH FIG. 5Cc

FIG. 5Cc

MATCH WITH FIG. 5Cb

GAAGAGCGAAGAAGACAAGGCGGCGAAGAGACGAGAGGGCTGAAGAGACGAGTTATTTTTCGGGTGTTGG

GGAGTGAGCCCCGCGGTCAGGAGGCTAACTGACTCAGCGGGC

GGTACCCGTGTATCCAATAAACCCTCTGCAGTTGCATCCGACTTGTGTCTCGCTGTT

CCTTGGGAGGGTCTCCTCTGAGTGATTGACTACCGTCAGCG

600

CCATGGGCACATAGGTTATTGGGAGAACGTCAACGTAGGCTGAACACCAGAGCGACA

AGGAACCCTCCCCAGAGGAGACTCACTAACTGATGGCAGTCGC

GGGGTCTTTCATT

---+--- 613

CCCCAGAAAGTAA

FIG. 5D

| | |
|---|---|
| FIG. 5Da | FIG. 5Db |
| FIG. 5Dc | FIG. 5Dd |
| FIG. 5De | FIG. 5Df |
| FIG. 5Dg | FIG. 5Dh |
| FIG. 5Di | FIG. 5Dj |
| FIG. 5Dk | FIG. 5Dl |
| FIG. 5Dm | FIG. 5Dn |

MATCH WITH FIG. 5Db

FIG. 5Da

```
CTAGCTTGCCAAACCTACAGGTGGGTCTTTCATTCCCCCTTTTCTGGAGAC
ATTTATCTATGGCTCGTACTCTATAGGCTTCAGCTGTGATATTGTTGAGTCA
TAATCGATTGAGAATGCAAGGTCCAAAGAGTAAGATCAGTAAGAGTACTATTAG
TTAAACAGCCCTTCGAACCATCCTTGGCCTGTCTCAAATAGTTTTTGTCTCTGA
TGTGGTCTGCATAAAAACAACATTCTCTTTTAGGGCTGCGCAGAGACCTCCCT
TTCAGACAACGAGGTCAGTGACTTTTCTAGGTTGGTAATTGACTTT
GTTTTAATTAAGGCAGTTAGCTGGGGCCAGAGGTATGGTTGGAGTAAGTACCTAGGACG( CAATCCCCTCCCATG
TTTTATATTGTTACGCTGTTCAAGCTGACCATACATATAATCGGG
TAGATTGAGTACAGTAGTAGATAGGCAGGAGTAGGCCGGTGTTG
TTTTGGGTGGTATTACACAGGGCCCTGATGGGTTTTGGGAACTGCTC
CCGCGGGAGCAGTTAGCTGGGGCCAGAGGTATGGTTGGAGTAAGTACCTAGGACG(
CTCTTGGGTTTTGTCAGGACTGGTGAGGTTGAGTGCTTGGTATGCTCCATCTAC
GCAGTCCCAGGACCATAGAGGCTGCGCCTGTAGGAGGAGTCTGAGGAGGCCTG
TCACGGGATTAGGCCCAATGGGATGCGGGGCCCTATATTGAGGACCTGGGGG
```

MATCH WITH FIG. 5Dc

FIG. 5Db

TAAATAAAATCTTTT

AAACTAGAGCCTGGACCACTGATATCCTGTCTTTAACAAATTGGAC

AGGTCCCATGATGGTGGAGATTAAGGTGGTAAACCAGGGGATCTA

TTAAGCCTTTCTCTTAATTGGCCATGCTGTCTCTCACTAGCCCCG

CCTTTAGGAATAGCAAATCTAGGCCCTCTGCGGTTCTGTAGGACTAC
TCGACTTCGTTGAGGTCTGTCTGGATAGCGGCATGAAGCTGCTCAAACTGCTGG

GTTAATCCTCCTAGTAGAGAAGGGCCAGGTCAATGATACTGGCTCTC
GGAGTGGTAAATTACTCTGGGCCAGAGTTCAACTAATACACAATAATCTGTGT
CAAGCCCAAATGGTCCCGGCGGAGCAGCCAGATAGTAGGACCCGTCGCTCGTC
CTACGCAGAGTCCCTGTCCCGGTTACTTCGGACAGGGTCAGCTTCAGTTGGGAGG

CAACCCCTTCGTAGTAGGGGGTCCCGATACCAGACACAACCAGCA

CAGGTTTAGCAGCCTGTCTCCCCGTCCCAGGTTGTTGAGACGGTGGG

GGGAGCCTGATCTGCACGGGTCGGGAGGGGGTAGTTGGCCAGTGA

TCAAAGAGAACCGGGTCACCGGGTCGATCCCTGTGGATTGGTACAG

MATCH WITH FIG. 5D d

MATCH WITH FIG. 5D a

FIG. 5Dc  MATCH WITH FIG. 5D.a

MATCH WITH FIG. 5Dd

TCTTAGTCCCCATACTTTGGGGCCATCCCAGCTGGCCTTTTTACCCGCGTCAGT
TGGATGCCACTGGAGACCACTGAGGAATCATAACAGGGCCCTGATTCCGAGGG
TCCAGTATGCCTGTCCAGTGGTCTCACAGCCCCATTGCCACAGTAGCCCTCTC
GAAGTCAAATGTTCTTGCCCGTTTCTTCCCCCGGGAGTGCGACACCCAAGTCC
AGCATAGGAAAGGCATCTGTCATTGTCCCCAGGAGGAGGTAGCGT
GGTGAGGGCTGTCATGTTGTACTGATACTCCTGCCCTTATTAAGATCCCCAGGA
GAACGCTGGACCTTCCATGTCGGTCCTGATGCTGTTCCGGCCGGAGGGGTTGTC
CTTTGAGAGCGGTGGGGTGGTCAGCAGGACGGTATAGGTCCTTTCCAACGAG
GACACGGAAGGGGTGTGGTATCACTGGCTGGTCTTGCTGGTCCTGATAGGCCGC
AAGTGAGCTTGGAGAGAGGGCTGTTAGTAACTCTGGTCATGTCAGGGTCAGGG
TGAGGCCATGGGGGCCCGGCGTGTTGCGGGCTCGGTACAGGGCTAAGGGGAGTA
AGTCTCCTTGATGGTCCTATTCATTCTTTCTACCTGACCTGAGCTTTGGGGTCT

MATCH WITH FIG. 5De

FIG. 5Dd

MATCH WITH FIG.5Db

```
GAATTCTAGGACTAGGGGATTGCATCGACCCCCGTGTGGCACCC
GTGTTTCCTCGCTTAAGGGAAATTAGGTCCCATGATGATGGCT
TCGGCCCTCCACACCCTGTTGGTACAGTATGCCCGGGCAAACATA
AGTCTCATCCCAATCGTCCCCTATTAAATCGCACAAGTCGAAGTAC
TAGCTGTTTGTCCTGTCATTAAGTTGGTAACTCTCCAAGTAACATTGAAGACCT
CTATCAGGGGCCCCACGGGTTAATCTTATCTTTAAGGGGTTTTGA
GCCGCCTTTACGTGAGCGGTGGATCCACGCCAGGCGATGCCGTCTA
GTTCCAAGTTCTTAGTCTCGTGGTCCGGCTACCCACACGGTGTCGCC
AGCCAGTGGCTTCCAGACCCTCTCGTTGTTACTGCTTGAAGGGCCTGT
AAGTTTACAAGGGCGGGGGTGCCCCATATAGATCTCATATGGGG
GGAGCACCCAGTCTCTAGAGCCAGTTGCAAGCGTTAATTTAGTTAA
GTATGCACAAATGTAATTCCAATCAATCCCCAACAGATCGGCCACT
```

MATCH WITH FIG. 5Df

MATCH WITH FIG. 5Dc

MATCH WITH FIG. 5Df

FIG. 5Da

GTCTGACTCACCTTGGAGAGACGAAGGCAGGCCCATTGTCAGTTCCCAATACCTGC
CGACCTTGGCGGTTTCTTTCTTAGTTGGGAAAGCTTCTATCCAGCC
TACCTCGGTGAAATCGATCTCCCCAGTGTGCCAGGCCGATGCCCGCGGACCCT
GCTTTGCAGGTCTCAGTGATATTTTTGAGTGTTCGATCCCGGTTCAGCATGTAG
TGAGGTGGGTCAATTGGTGAAGAAAGTCTAGTAACTCAAAGGTGAATTGATCAG
ATAAGTGGCTCCCTAGTTTGGTCAAATCCTTTGTGTCAGTTACTGTATAGTGAAA
GTTCCTGGAGTTTCTCTAGTGGCTACTTCTCGGGCCGCTTGGTCGGCCATCCGG
GAATTATGCTAAGTCTTTTGGGCAAGAGAGCCTTTAGTAGGGCTAAGATCT
CCTTCTGTATATTTCTCCATGAATATGGGGGTGGCAAAAGCGTAACGGCTATC
GTGAGCGCTATCAGTTCAGCTCTTTGGGCCGATGTCCCGGCTGCAATGCCCTG
GCTGCCCTTCTTGCAGGAAGCTGCTCCCATCCGTGTACCAGTGTGGTCGGCGT
AGCCAAGATGTCAAGGCAGTCATGTTGCAGCCCCTCCTCAGGCAGAGGGAGCAG

MATCH WITH FIG. 5Dc

MATCH WITH FIG. 5Dg

FIG. 5Df

MATCH WITH FIG. 5Dd

```
GGCATGCCGAACCTAGGAAGATCTCTTCTAGCAGTTTCTTGGTCA
AGAAAAAGTATCTACAAAAACTAAAAGATACTTATAGCCATACAATCCAGGTTT
AGTTCCTTGCTTAACGGCAGACTTGCTGGCATTGACTTGTGCACAA
TAGGGACTGGGGCTTCTCTCTAGGAGAGCCCTTTGTTTTTGAGAAGC
GCATAACAGGCTTTCCTTGATAGACCCAATATTTCTTCGCACTGTC
GTGTTCATGGGTATAGGGGTTGAGTTTCTATCAGAAGTGTGGAA
TTGCCCCTGGCCTCTGCGCCTGTTTCCTTTTGATGTCCCGGGCAAT
CGTCCCTTGTTCTTGATCTCTTTTCCTTCTGATGTGAGCAACCCGCG
AGTATAAACATTTAGCTTCTTCTTACCTTCTGCCATCTTTAGGCTTGG
GCCCAGATTACCTCAGTCTCAGTGGTCCGTAAGATCTGATCTAGTTCCGTGGCTTC
CTGGGAGGGCTGGTCCGTAAGATCTAGTTCCGTGGCTTC
CGTAGCTGGATTTAGGGCCACTACTGSCCCGAACTGGACCCGGTCC
```

MATCH WITH FIG. 5Dh

MATCH WITH FIG. 5De

FIG. 5D9

MATCH WITH FIG.5De

MATCH WITH FIG. 5Dh

```
GTGTCCAGGAGCAGGGGCTTGGTAATGGGTCATCCGGGCATTGGAGAGCCAGCGA
TGACCAACGGCTGTCCCATAGTGAGCTTGCCAGCATCTTTGTCAGAACTGCAA
GTCTAGCTTTTTAGACAGGTAGGCCACCGGCCGACGCCAAGGTCCCAGCTTTTG
TCAAAGGGCTTAGTCAAATCTGGCAACCCCAGGCTGGGGCAGTTAGAAGAGCT
ACAGAGTCCCCGTTTTGGTGAGAGGGTACAAGGGGCTGCCATTCTGCAAACC
TAGTTGTCGAGGGGTCTTCGGAGTAGGCTGCCCCATCACAGTCTCT
TTGACCTGTTTCTGGCAAATTGGGCTTTCTTGGCCGAGGCCCGATACCCGAGG
GCTCAGAAGTGGCGGCCAGCAGTAAGTCATCCACGTACTGTAGCAGGATCAAGT
ATCAAACAGGGTGGGACTGTTTTGAAACCCTGTGGGAGTCTCGGTCCAGGTCAA
AGAGGCTGACTGGGGTGGAGTCTCAGGCAGAAAAGGCATCCTTTAAATCA
TGTAAGGGTTGGGCACGGTGGGGTGGATGTCTTCCACCCGCTTGTTGACTTCTC
GGGTAGCAGGGGCGTGTTCCAGGGGACTGGCAGGGTACCAGTATTCCCCTGGTC
```

MATCH WITH FIG. 5Di

FIG. 5Dh

MATCH WITH FIG. 5Df

TCAGGGGGTTGCTTAACTAGTGCCTCTACGGCATGGGGGCCAGAA
TGGCTGCCACCATCCGTAGGCAGGGGGCCAGCCAGCTGCCACTGG
CGTTAGGACGCCTTTGGCGTAGCCCTGCTTCTCGTGACAAAGAGT
TGCTTGATTTCTTGATAGGCCTTTTGTTGGTCTGGGCCCCAATTAA
CAGGGATCCAGAGGCGACAGAAGCCTGCCGTCCCTAGGAACTCCCT
TTTCTCGGCCTCAGTCAGCCATCTCTGACCCTCTTTTAGAAGATACCCCAGATAC
TTCCCTAGGGTTTGTAACAGGGCCCGAGTACCTTGTTGGCAGTCTA
CTGGGTGCTGGATCCGGAAGTCTGCTAGTCTCTGTGCAGTGCCTC
TTGTCCTGAGATTCCCATCTCTGGATCTCTCCACTCAAAGGCGAAG
AGCACAGTGTACCACTGGTGGGACGGTGGGAGCCCGCTCAAGAGGT
TCAGATCCTGGACAGGCCTATAATCATTAGTCCCTGGTTTCTTAAC
CAACAGTCTCTGTATGTGGGCTTGATCCCCAGTCTGGCTTCTTGT

MATCH WITH FIG. 5Dj

MATCH WITH FIG. 5Dg

MATCH WITH FIG. 5D j

FIG. 5Di

MATCH WITH FIG. 5Dg

MATCH WITH FIG. 5D k

```
GACATGGGGTATTGTTTTATGGACACGGGGGGTAGAGGTTGCTTTCAGAGGTAT
CCCAGGCCTGAGGAAAATCAGACAGCCATGTGGACCCTAGAGAAACATCTGGC
CAACACTTGCAGGGGCTGCCCCATTGGTCCCATAACCTGAGCTCCTGATCCCT
AGAGGATAGGGACAGTCTGGTACATGGAGGAAAGAGTGGGTGACCTTACCGGT
CAGTAGCCCCCTTGGACCCAGGCAGACTTATCACTTAGGGGTCCAGGATTTTGG
TTGCCCCCCGACTTTGAGGGTTATCCTGGGTTCAGGGGGGGCTCCCTGACCCT
CCCCGAGGTCCTCGTGGTTTCTGTGTTCTGTCCACTAACGACAGTGGCCCCTTTC
CTCCCTCCCTGTCTATCCTGTTCTCTTCCACTAACGACAGTGGCCAATAGCTTG
ATCCTCTGTCCTACGGCGTTCTCTTTCCTCTGTTCTCTCCTGATACGTT
TCTCTAACCAAATCTCCAAGCGTCTTGTTTTTAAATCTTCTAACCTCTCTAA
CATTAGTTTCTTGCCCTGGGTCCTCAGGGTCATAAGGAGTGTACCTGCGATAG
TTGTGTTATTCCTTTTACCTTGGCCAAATTGGTGGGGCTTCTGCC
CCTGCCTGGGTGGTAATCCCAGTCCCAGTCTGGGCGCTCGAGGGGAAAA
```

FIG. 5Dj

MATCH WITH FIG. 5Dh

GATCAGAGGAGCTTGGCGAACTGCCAGTCCCATGCCCCGGTTTCCG
TCTTTGAGGTCTCATGTAGCCGATACTCATCTTCTATATTTAGGGT
CAAAGTGGATTTGGGCTTTTAGTTTAGTCAGCAAATCTCTTCCTAAC
AGCTAGATGTACTTTGCGATCCGTGGTCCAGCGATACCGCTTTCCTC
GTCAGCACGGAGTGTTGGGCCCCAGTATCTACCAGGAAGGTGACGGG
GACCTCCCTAGTCATCTAGGGTCAGGAGGAGGTCTGGGGTCTTGGT
TTTGCAGTAGGCACACTGGTCGCGATCGAGTTGGGACCTCCTTCGTT
CTCATCTCTCTATGTCTCCTACGATCTCTTTCTTTCTTTCTGCTC
CCTCTCTTTCTTCCGGGTTTCTCTGCTTTATTAAAGATCTTTCTGCC
CTTTCTCCCAATGTCTGGGGCAGACTGCCAAATGAAAGACATAGACA
GCTTCCTTAAGTCTCTCTAGGAAGGCCGAGGGAGACTCATTGGGCCC
CGGGTTTGGAGACCCGCTAGGAGCAACTGGCGATAGTGGACTAGGTGGTTCCTA
GCGGCATCGACTTCATTGGGCCAGTTGAGTGGGGCGCCATCATGCGCCCCGCACCG

MATCH WITH FIG. 5Di

MATCH WITH FIG. 5Dl

MATCH WITH FIG. 5Dl

FIG. 5DK

MATCH WITH FIG. 5Di

CCTTTCTAGCCTCTAAGAGAGCACCCGTTGTTTTCTTCCGGTCAGCAGAGTC
AACAGACTCGATCAGAGCTGTCAGTTTACCTGGATCTTCAGAAAAGAAGGGT
TGAAGCTGTCCGTTCCTCCTGCGGGAGGGGAATGCCTGCGAGGTAGTGGA
GGGAGGGGTCCGGTGCCTCTCCCGCAGGGGTCGCTTCTCCACCATTTCCGTCC
TGTAAGTAGGTCGATGAGCGGGCCCCCCACTGTCAGAAAGAACTTGAGGTTAG
GGCGGGGTCGAACGAGGAGTTCAAGGGGAGAGACGGGCCGATGCGAGGAAG
GGTCAAAAGCCAAGGCTTCCCAGGTCACGATGTAGGGGACCTGGT
GTCTCGGTTAAAGGTGCCGTCTCGGCCATCCGATGTTAAAGGTTGGCCATT
TGGTTGTGAGCGATCCGCTCGACATCTTTCCAGTGACCTAAGGTCAAACTTAA
CAGTCAGACAGAGACAACACAGAACGATGCTGCAGCAGACAAGACGCGGGCG
CTGTTTTTAGGTTCTCGTCTCCTACCAGAACCACATATCCCTCCTCTAAGGGGG
GCCACAAAAACGGGCCCCGAAGTCCCTGGGACGTCTCCCAGGGTTG

MATCH WITH FIG. 5Dm

FIG. 5Dl

MATCH WITH FIG. 5Dj

```
CCCAACAGCTGCTGACAGTCGTCCCAGTGGGCTGATGGGTGATGAG
TATTATTTTCCAGTTGTAAAGGTCAGAAGAGGAGAACGGCCAGTAT
GTCGGCCACAGGGGGGCTCCCCGTCTCCCACGTAGGCGAGATGCCATTG
CTGTCGGAAGGGGGTGGTCTTGGGTCCCTATAAGGCGGGGGGTCTTC
GTTTGGGCGCCTAGAGAAGGAGTGAGGCTGGATAAAGGAGGAGCGA
AGGAGGCGGAGGCTTAGGGTGTACAAAGGCTTGACCCAGGGAGGGG
CTGGGTGTCCATGCGGGCCAGGTGAAAAGACCTTGATCTTAACCTGGGTGATGAG
CTGCAGAGCAGAAGGTAACCCAACGTCTCTCTTGACATCTACCGAC
GGGAGTGGTAACAGTCTGGCCCATTTTTCAGACAAATACAGAAACA
CGGCTTCGGTCCCAAACCGAAAGCAAAAATTCAGACGGAGGCGGGAA
GTGCACCAAAGAGTCCAAAACGATCGGGATTTTGGACTCAGGTCGG
CGGCCGGGGTGTTCCGAACTCGTCAGTTCCACCACGGGTCCGCCCAGATACAGAGC
```

MATCH WITH FIG. 5Dn

MATCH WITH FIG. 5Dk

MATCH WITH FIG. 5D n

FIG. 5D m

MATCH WITH FIG. 5D k

TAGTTAGTAACTAGTACCGACGCAGGCGCATAAATCAGTCATAGACACTAGA

GGTGGGTCGGTGGTCCCTGGGCAGGGTCTCCCGATCCCCGGACGAGCCCCAAA

CCAAGGAACAGCGAGAACCACACAAGTCGGATGCAAGAGGGTTATTGGAT

AGTGAGGGTTGTGGGCTTTTTTATTGAGCTCGGGGAGCAGAAGCGCGCGAACA

CATTTCAGGTCCCTGGGGCACCCTGGAAACATCTGATGGTCTCTAGAAACTGC

CGGGGCAGGAACTGCTTACCACAGATATCCCTGTTTGGCCCATATTCAGCTGTTC

GGGCAGGAACTGCTTACCACAGATATCCCTGTTTGGCCCATATTCAGCTGTTCCA

TTTTCCATGCCCTTGCAAAATGGGCGTTACTTAAG

FIG. 5Dn

MATCH WITH FIG. 5Dl

CAATCGGAGACACAGATAAGTTGCTGGCCAGCTTACCTCCCGGT

TGAAAGACCCCCGCTGAGTAGTCAATCACTCAGAGGAGACCCTC

ACACGGGTACCCGGGCGACTCAGTCAATCGGAGGACTGGCGCCCCG

GAAGCGAGAAGCGAACTGATTGGTTAGTTCAAATAAGGCACAGGGT

TGAGGGCTGGACCGCATCTGTTCTTGGCCCTGAGC

CATCTGTTCTTGGCCCTGAGCCGGGGCAGGAACTGCTTCTGAGCCG

TCTGTTCCTGACCTTGATCTGAACTTCTCTATTCTCAGTTATGTAT

MATCH WITH FIG. 5Dm

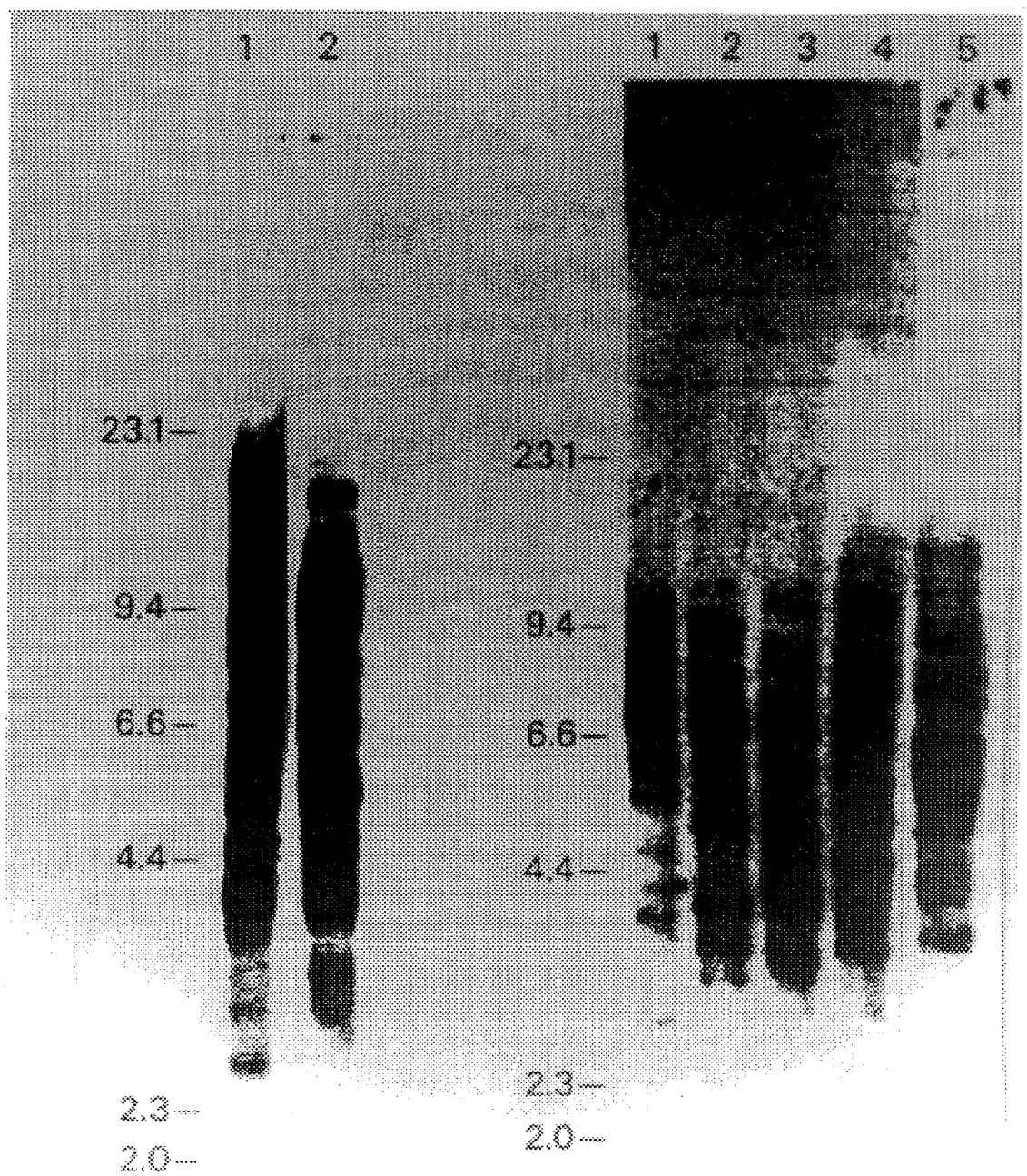

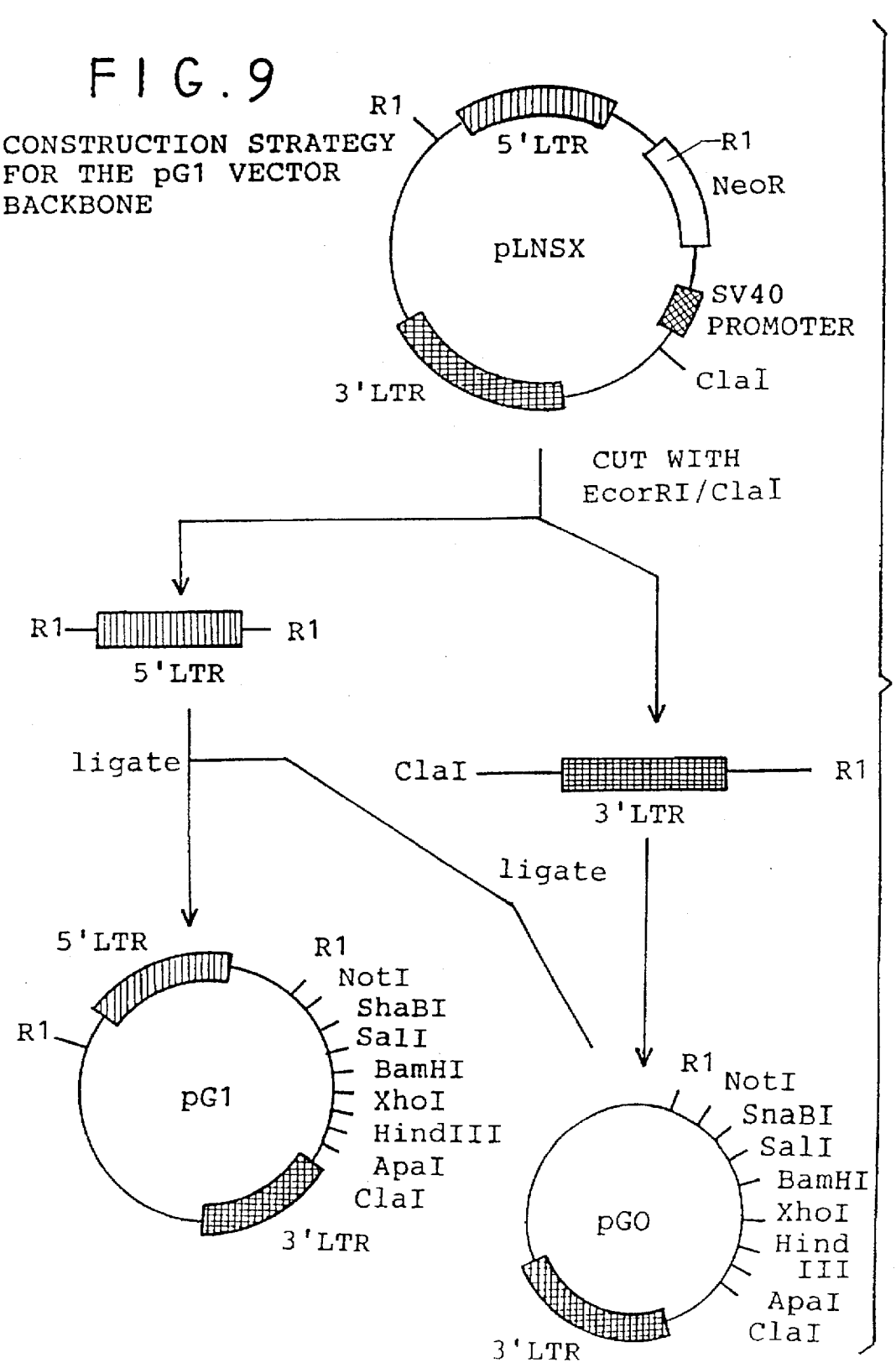

SEQUENCE OF THE MULTIPLE CLONING SITE IN THE pGI PLASMID

| 1/2 EcoRI | NotI | SnaBI | SalI | BamHI | XhoI | HindIII | ApaI |
|---|---|---|---|---|---|---|---|
| AATTC | GCGGCCGC | TACGTA | GTCGAC | GGATCC | CTCGAG | AAGCTT | GGGCCC |
| G | CGCCGGCG | ATGCAT | CAGCTG | CCTAGG | GAGCTC | TTCGAA | CCCGGG |

1/2ClaI

AT

TAGC

FIG. 10

RETROVIRAL VECTOR PARTICLES

BACKGROUND OF THE INVENTION

This invention relates to retroviral envelopes and LTRs, and retroviral vector particles including such envelopes and/or LTRs. More particularly, this invention relates to novel retroviral envelopes and LTRs which may be employed to generate retroviral vector particles.

Retrovirus-mediated gene transfer has become one of the most widely applied methods for introduction of genes into primary cells. (Linial, et al., *Curr. Top. Microbiol.*, Vol. 157, pgs. 124–152 (1990); McLachlin, et al., *Prog. Nucleic Acid Res. Mol. Biol.*, Vol. 38, pgs. 91–135 (1990); Miller, *Curr. Top. Microbiol. Immunol.*, Vol. 158, pgs. 1–24 (1992); Miller, et al., *Biotechniques*, Vol. 7, pgs. 980–990 (1989)). This method already has been used successfully for clinical investigation and therapeutic applications. (Blaese, *Pediatric Res.*, Vol. 33, pgs. 549–553 (1993); Brenner, et al., *Lancet*, Vol. 342, pgs. 1134–1137 (1993); Brenner, et al., *Lancet*, Vol. 341, pgs. 85–86 (1993)).

Attractive features of retroviral vectors include flexibility, that is, the variety of coding sequences that can be transferred, high although variable transduction efficiency, and stability of the proviral genome once integrated into a host cell chromosome. The greatest concern about the use of retroviral vectors for clinical applications has been their potential to induce or contribute to the neoplastic transformation. This concern was enhanced by the development of rapidly progressive, fatal lymphomas in three nonhuman primates subjected to autologous transplantation with retrovirus-transduced bone marrow cells. (Donahue, et al., *J. Exp. Med.*, Vol. 176, pgs. 1124–1135 (1992)). The disease pattern, latency period, and high titer of replication competent retroviruses in the sera of these animals are highly reminiscent of the features of retrovirus-induced lymphomas in rodent species (Tsichlis, *Curr. Top. Microbiol. Immunol.*, Vol. 171, pgs. 95–171 (1991)).

The packaging cell lines that constituitively synthesize retroviral proteins, and the vectors in current use were derived from components of various proviral genomes. (McLachlin, et al., 1990; Miller, 1992; Miller, et al., 1989.)

Packaging lines that yield viruses with ecotropic specificity are based on components of the Moloney murine leukemia virus (Mo-MuLV), whereas amphotropic packaging lines were engineered with the envelope gene from the 4070A virus, a naturally occurring murine retrovirus with amphotropic host range. The retroviral vectors and packaging components used to develop producer clones for clinical applications have been designed to minimize the potential for mutational events that could give rise to a replication-competent retrovirus.

(Danos, et al., *Proc. Nat. Acad. Sci.*, Vol. 85, pgs. 6460, 6464 (1988); Markowitz, et al., *J. Virol.*, Vol. 62, 1120–1124 (1988); McLachlin, et al., 1990; Miller, 1992; Miller, et al., *Mol. Cell. Biol.*, Vol. 6, pgs. 2895–2902 (1986); Miller et al., 1989; Miller, et al., *Somatic Cell Mol. Genet.*, Vol. 12, pgs. 175–183 (1986)).

Methods developed in murine models for developing strategies for gene transfer into repopulating hematopoietic stem cells have been applied with varying success. Bodine, et al., *Proc. Nat. Acad. Sci.*, Vol. 87, pgs. 3738–3742 (1990), found that rhesus monkey stem cells could be transduced by using a high-titer amphotropic producer line that generated an estimated $10^{10}$ infectious vector particles per ml of culture medium. The vector used, N2, has two regions of sequence identity with the RNA transcript in PA317 packaging cells that encodes the retroviral structural proteins. The high-titer amphotropic producer clone used for the stem cell transfection experiments had been developed by ping-pong amplification between a lower-titer PA317 producer clone and the GP+E86 ecotropic packaging line (Bodine, et al., 1990).

Such coculture of amphotropic and ecotropic producer cells is also likely to amplify any replication-competent virus that arises by recombination between vector and packaging RNA transcripts. (Bestwick, et al., *Proc. Nat. Acad. Sci.*, Vol. 85, pgs 5404–5408 (1988).)

The high-titer N2 producer cell line was shown to generate replication-competent retroviruses with a titer of approximately $10^4$/ml of culture medium. (Bodine, et al., 1990.)

Early safety studies had suggested that amphotropic MuLV of the type likely to be generated in the N2 producer clone was nonpathogenic, either when infused intravenously or when derived from infected, autologous fibroblasts transplanted subcutaneously. (Cornetta, et al., *Human Gene Therapy*, Vol. 1, pgs. 15–30 (1990); Cornetta, et al., *Human Gene Therapy*, Vol. 2, pgs. 215–219 (1991).)

However, 3 of 10 animals that received autologous bone marrow cells transduced with preparations from the high-titer N2 producer line developed a rapidly progressive T-cell lymphoma involving the thymus, lymph nodes, liver, spleen, and bone marrow. (Donahue, et al., 1992.)

Replication-competent retrovirus was found in the sera of two animals studied, and between 10 and 50 copies of a proviral genome were present in DNA from tumor tissues of each of the three animals.

It is an object of the present invention to obtain nucleic acid sequences encoding a viral envelope protein and the viral LTR from viruses found in the serum of animals in which tumors developed subsequent to infection of such animals with retroviral vector particles, and to employ such nucleic acid sequences in forming viral vector particles and producer cell lines.

DETAILED DESCRIPTION OF THE INVENTION

In accordance with an aspect of the present invention, there is provided a nucleic acid sequence encoding a retroviral envelope. The nucleic acid sequence encoding said retroviral envelope has the nucleic acid sequence of (SEQ ID NO:8) or a sequence which hybridizes to the sequence of (SEQ ID NO:8) under conditions of high stringency. Such sequence includes MCF, amphotropic, and xenotropic envelope portions.

The mink cell focus forming, or MCF, sequences of the envelope sequence of (SEQ ID NO:8) are at the N-terminal two-thirds of the gp70 segment of the envelope. A xenotropic segment immediately follows the MCF sequence with the amphotropic sequences immediately after the xenotropic sequence. The nucleic acid sequence encoding p15E protein is identical to that within pPAM3 (Miller, et al., *Mol. Cell. Biol.*, Vol. 6, pg. 2895 (1986)) with the majority being amphotropic and the extreme C-terminal end being ecotropic.

Such a nucleic acid sequence may be used to construct a packaging plasmid including the nucleic acid sequence as of (SEQ ID NO:8), which encodes a first retroviral envelope portion which is a portion of MCF gp 70 protein, a xenotropic envelope portion, an amphotropic envelope portion, and a retroviral envelope portion which is p15E protein.

Such a plasmid may be constructed by genetic engineering techniques known to those skilled in the art. For example, a packaging plasmid including DNA (RNA) encoding amphotropic gp70 protein, and DNA (RNA) encoding p15E protein, the majority of which is amphotropic and a portion of which is ecotropic, may be engineered such that a portion of the DNA (RNA) encoding the retroviral envelope is removed and replaced with the nucleic acid sequence of FIG. 5A. Such a packaging plasmid may be transfected into a packaging cell, thereby producing a packaging cell line including DNA (RNA) encoding the retroviral envelope hereinabove described. Such packaging cell line also may be transfected with a retroviral vector which lacks one or more of the structural genes of the virus. Such retroviral vector may include at least one nucleic acid sequence encoding a therapeutic agent. The term "therapeutic" is used in a generic sense and includes treating agents, prophylactic agents, and replacement agents.

Genes encoding therapeutic agents which may be placed into such retroviral vector include, but are not limited to, tumor necrosis factor (TNF) genes, such as TNF-α; genes encoding interferons such as Interferon-α, Interferon-β, and Interferon-γ; genes encoding interleukins such as IL-1, IL-1β, and Interleukins 2 through 12; genes encoding GM-CSF; genes encoding adenosine deaminase, or ADA; genes which encode cellular growth factors, such as lymphokines, which are growth factors for lymphocytes; genes encoding soluble CD4, Factor VIII, Factor IX, T-cell receptors, the LDL receptor, ApoE, ApoC, the alpha-1 antitrypsin (α-1AT) gene, the ornithine transcarbamylase (OTC) gene, the CFTR gene, Fc receptors for antigen-binding domains of antibodies, the insulin gene, and antisense sequences which inhibit viral replication, such as antisense sequences which inhibit replication of hepatitis B or hepatitis non-A non-B virus.

Such genes are under the control of a suitable promoter. Suitable promoters which may be employed include, but are not limited to, adenoviral promoters, such as the adenoviral major late promoter; or heterologous promoters, such as the cytomegalovirus (CMV) promoter; the Rous Sarcoma Virus (RSV) promoter; the respiratory syncytial virus promoter; inducible promoters, such as the MMT promoter, the metallothionein promoter; heat shock promoters; or the gene's own natural promoter. It is to be understood, however, that the scope of the present invention is not to be limited to specific foreign genes or promoters.

The retroviral vector may also include an appropriate selectable marker. Examples of selectable markers which may be employed include, but are not limited to, the neomycin resistance (neo$^R$) marker, the ampicillin resistance (amp$^r$) marker, the hygromycin resistance (hygro$^R$) marker, the multidrug resistance (mdr) gene, the thymidine kinase (TK) gene, the β-galactosidase (β-gal) gene, the dihydrofolate reductase (DHFR) gene, and the chloramphenicol acetyl transferase (CAT) gene. It is to be understood, however, that the scope of the present invention is not to be limited to any specific selectable marker.

Upon transfection of the packaging cell with the packaging plasmid and the retroviral vector, the packaging cell may generate infectious viral particles, including an envelope encoded by the nucleic acid sequence of FIG. 5A, in which the envelope includes MCF, amphotropic, and xenotropic envelope portions. Such infectious viral particles then may be employed in transducing eukaryotic cells, which may administered to a host as part of a gene therapy procedure.

Eukaryotic cells which may be transduced with the infectious viral particles include, but are not limited to, primary cells, such as primary nucleated blood cells, such as leukocytes, granulocytes, monocytes, macrophages, lymphocytes (including T-lymphocytes and B-lymphocytes), totipotent stem cells, and tumor infiltrating lymphocytes (TIL cells); bone marrow cells; endothelial cells; epithelial cells; keratinocytes; stem cells; hepatocytes, including hepatocyte precursor cells; fibroblasts; mesenchymal cells; mesothelial cells; and parenchymal cells.

In one embodiment, the cells may be targeted to a specific site, whereby the cells function as a therapeutic at such site. Alternatively, the cells may be cells which are not targeted to a specific site, and such cells function as a systemic therapeutic.

The cells may be administered in combination with a pharmaceutically acceptable carrier suitable for administration to a patient. The carrier may be a liquid carrier (for example, a saline solution), or a solid carrier such as, for example, an implant or microcarrier beads. In employing a liquid carrier, the cells may be introduced intravenously, subcutaneously, intramuscularly, intraperitoneally, intralesionally, etc. In yet another embodiment, the cells may be administered by transplanting or grafting the cells.

Transduced cells may be used, for example, in the treatment of cancer in a human by transducing into human primary cells, such as, for example, blood cells, which specifically "target" to a tumor and which have been removed from a cancer patient and expanded in culture, infectious viral particles in accordance with the present invention which contain genes that enhance the anti-tumor effects of the blood cells. The blood cells can be expanded in number before or after transduction with the infectious viral particles containing the desired genes. Thus, the procedure is performed in such a manner that upon injection into the patient, the transformed blood cells will produce the agent in the patient's body, preferably at the site of the tumor itself.

The gene carried by the blood cells can be any gene which directly or indirectly enhances the therapeutic effects of the blood cells. The gene carried by the blood cells can be any gene which allows the blood cells to exert a therapeutic effect that it would not ordinarily have, such as a gene encoding a clotting factor useful in the treatment of hemophilia. The gene can encode one or more products having therapeutic effects. Examples of suitable genes include those that encode cytokines such as TNF, interleukins (interleukins 1–12), interferons (α, β, γ-interferons), T-cell receptor proteins and Fc receptors for antigen-binding domains of antibodies, such as immunoglobulins.

Additional examples of suitable genes include genes that modify primary cells such as blood cells to "target" to a site in the body to which the blood cells would not ordinarily "target," thereby making possible the use of the blood cell's therapeutic properties at that site. In this fashion, blood cells such as TIL cells can be modified, for example, by introducing a Fab portion of a monoclonal antibody into the cells, thereby enabling the cells to recognize a chosen antigen. Likewise, blood cells having therapeutic properties can be used to target, for example, a tumor, that the blood cells would not normally target to. Other genes useful in cancer therapy can be used to encode chemotactic factors which cause an inflammatory response at a specific site, thereby having a therapeutic effect. Other examples of suitable genes include genes encoding soluble CD4 which is used in the treatment of AIDS and genes encoding α-antitrypsin, which is useful in the treatment of emphysema caused by α-antitrypsin deficiency.

The transduced cells of the present invention are useful in the treatment of a variety of diseases including but not limited to adenosine deaminase defthalassemsickle cell anemia, thalassemia, hemophilia, diabetes, α-antitrypsin deficiency, brain disorders such as Alzheimer's disease, phenylketonuria and other illnesses such as growth disorders and heart diseases, for example, those caused by alterations in the way cholesterol is metabolized and defects of the immune system.

The transduced cells may be used for the delivery of polypeptides or proteins which are useful in prevention and therapy of an acquired or an inherited defect in hepatocyte (liver) function. For example, they can be used to correct an inherited deficiency of the low density lipoprotein (LDL) receptor, and/or to correct an inherited deficiency of ornithine transcarbamylase (OTC), which results in congenital hyperammonemia.

For example, hepatocyte precursors transduced with infectious viral particles of the present invention may be grown in tissue culture vessels; removed from the culture vessel; and introduced into the body. This can be done surgically, for example. In this case, the tissue which is made up of transduced hepatocyte precursors capable of expressing the nucleotide sequence of interest is grafted or transplanted into the body. For example, it can be placed in the abdominal cavity in contact with/grafted onto the liver or in close proximity to the liver. Alternatively, the transduced hepatocyte precursors can be attached to a support, such as, for example, microcarrier beads, which are introduced (eg., by injection) into the peritoneal space of the recipient. Direct injection of the transduced hepatocyte precursors into the liver or other sites is also contemplated. Alternatively, the transduced hepatocyte precursors may be injected into the portal venous system or may be injected intrasplenically. Subsequent to the injection of such cells into the spleen, the cells may be transported by the circulatory system to the liver. Once in the liver, such cells may express the gene(s) of interest and/or differentiate into mature hepatocytes which express the gene(s) of interest.

The transduced cells of the present invention may be employed to treat acquired infectious diseases, such as diseases resulting from viral infection. For example, transduced hepatocyte precursors may be employed to treat viral hepatitis, particularly hepatitis B or non-A non-B hepatitis. For example, an infectious viral particle containing a gene encoding an anti-sense gene could be transduced into hepatocyte precursors to inhibit viral replication. In this case, the infectious viral particle, which includes a vector including a structural hepatitis gene in the reverse or opposite orientation, would be introduced into hepatocyte precursors, resulting in production in the transduced hepatocyte precursors and any mature hepatocytes differentiated therefrom of an anti-sense gene capable of inactivating the hepatitis virus or its RNA transcripts. Alternatively, the hepatocyte precursors may be transduced with an infectious viral particle including a vector which includes a gene which encodes a protein, such as, for example, α-interferon, which may confer resistance to the hepatitis virus.

In accordance with another aspect of the present invention, there is provided a nucleic acid sequence encoding a retroviral LTR. The nucleic acid sequence has the sequence of (SEQ ID NO:12), or a sequence which hybridizes to the sequence of (SEQ ID NO:12) under conditions of high stringency. Such retroviral LTR may be constructed by standard techniques and may be employed in constructing a retroviral plasmid vector which also may include at least one nucleic acid sequence encoding a therapeutic agent. Such therapeutic agents may be those hereinabove described. Such retroviral plasmid vector then may be transduced into a packaging cell line including a packaging plasmid (which may, in one embodiment, include a nucleic acid sequence of (SEQ ID NO:8) which encodes the retroviral envelope portion) to form a packaging cell line which generates infectious retroviral vector particles, which include the LTR sequence hereinabove described as well as at least one nucleic acid sequence encoding a therapeutic agent.

Such retroviral vector particles then may be used to transfect eukaryotic cells such as those hereinabove described, and such eukaryotic cells may be administered to a host as part of a gene therapy procedure, also as hereinabove described.

In one embodiment, the at least one nucleic acid sequence encoding the therapeutic agent is under the control of the LTR promoter. Although the scope of this aspect of the present invention is not intended to be limited to any theoretical reasoning, such LTR promoter as hereinabove described provides for improved expression of genes under the control of such promoter.

The present invention also is directed to PCR primers for detecting MCF virus, and to PCR primers for detecting xenotropic virus. Such primers were designed by aligning previously sequenced MCF or xenotropic ENV genes, and then choosing sequences in conserved regions of the MCF and xenotropic ENV sequences.

In one embodiment, 5' PCR the primer for detecting MCF virus has the following nucleotide sequence:

GGACTYGGGTGTCGCACTCCC, wherein Y is a pyrimidine (SEQ ID NO:1). In another embodiment, the 3' PCR primer for detecting MCF virus has the following nucleotide sequence:

ACTGGAGACCRCTGAGGAATC, wherein R is a purine (SEQ ID NO:2).

In yet another embodiment, the 5' PCR primer for detecting xenotropic virus has the following nucleotide sequence:

GGATGACCCAGAACCCGATATTGG (SEQ ID NO:3).

In still another embodiment, the 3' PCR primer for detecting xenotropic virus has the following nucleotide sequence:

ATCATAACAGGGGCCCTGATCCTT (SEQ ID NO:4).

The present invention also is directed to PCR primers for detecting viruses having an envelope encoded by the nucleic acid sequence of (SEQ ID NO:8). In one embodiment, 5' the PCR primer has the following nucleotide sequence:

ATGATTCCTCAGTGGTCTCCAGTG (SEQ ID NO:5).

In another embodiment, the 3' PCR primer has the following nucleotide sequence:

TTCGTTGAGGTCTGTCTGGATAGC (SEQ ID NO:6).

BRIEF DESCRIPTION OF THE DRAWINGS

The invention now will be described with respect to the drawings, wherein:

FIG. 1 is a map of the potential recombination between the sequences in the N2 vector and packaging plasmid pPAM3 in PA317 cells to form a replication-competent virus;

FIG. 5A is a comparison of the env gene sequences of the virus isolated from clone 24 (SEQ ID NO:8) with MCF FrNx endogenous provirus (SEQ ID NO:7) and the V/H recombinant (SEQ ID NO:9);

FIG. 5C is the LTR sequence (SEQ ID NO:12) of the LTR of the virus isolated from clone 24;

FIG. 5D is the entire nucleic acid sequence of the virus isolated from clone 24;

FIGS. 7A and 7B are blots of genomic DNA of monkeys having tumors for V/H or AMP/MCF provirus;

FIG. 9 is a schematic of the construction of the plasmid pG1;

FIG. 10 is the sequence of the multiple cloning site in the plasmid pG1;

EXAMPLES

The invention will now be described with respect to the following examples; however, the scope of the present invention is not intended to be limited thereby.

Example 1

Figures 2A, 2B:
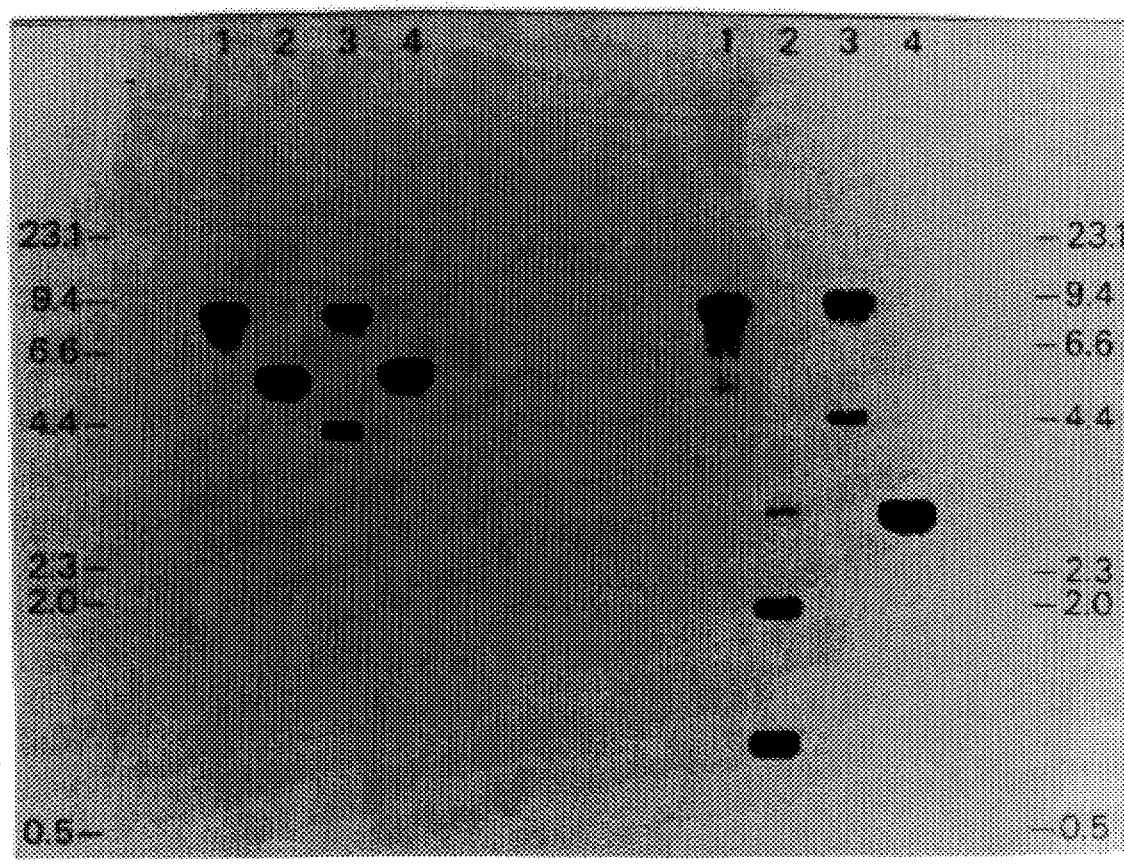
FIG. 2 (Panels A, B and C) depicts the results of Southern blot analysis of monkey tumor DNA performed with enzymes that would give fragment lengths predicted from the predicted restriction map of the replication-competent virus of FIG. 1.
Figure 2C:
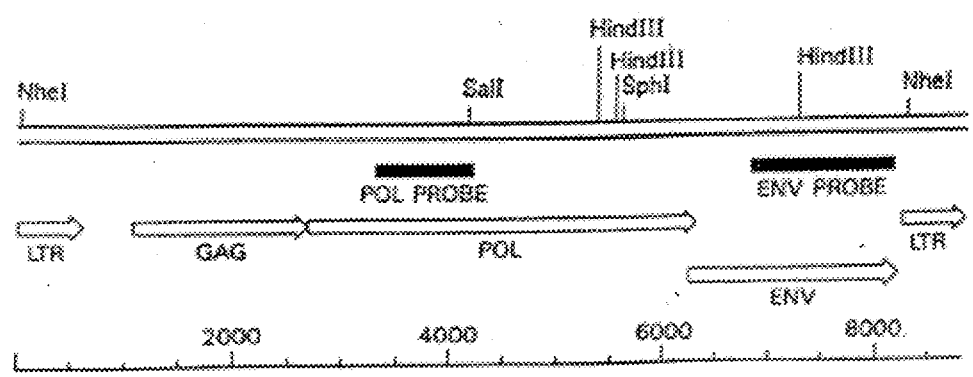

Based upon a hypothesis that recombination between an N2 vector transcript and an RNA transcript of packaging plasmid pPAM3 (Miller, et al., *Mol. Cell. Biol.*, Vol. 6, pg. 2895 (1986)) encoding viral proteins in PA317 cells had generated a replication competent virus as depicted in FIG. 1, Southern blot analysis of monkey tumor DNA was performed with enzymes that would give fragment lengths predicted from the restriction map of this vector/helper (V/H) recombinant provirus. (FIG. 2.) As shown in FIG. 1, the retroviral LTRs and neo$^R$ gene are shown as boxed areas. Ψ denotes the retroviral packaging signal. The two hatched areas between N2 and pPAM3 indicate the location and size of the regions of sequence identity. The double hatched area indicates the SV40 polyadenylation site from SV40. S.D. and S.A. in FIG. 1 indicate the position of the retroviral splice donor and acceptor sites, respectively.

The Southern blot analysis was performed by isolating the DNA from the monkey tumor tissue using SDS and proteinase K essentially as described by Maniatis, et al., *Molecular Cloning: a Laboratory Manual*, Cold Spring Harbor Laboratory, Cold Spring Harbor, N.Y. (1982). Following transfer and binding of the DNA to Hybond-N+ (Amersham Corp.), the filters were pre-hybridized for 2 hours in Hybrisol I (Oncor) at 42° C. Hybridization was done at 42° C. with 2 to $5 \times 10^6$ cpm of random primer labelled probe (Pharmacia)/ml of hybridization solution (Hybrisol I-Oncor) for 16 hours. The washes were done at 65° C., first with 3×SSC containing 0.5% SDS (2×,30 min.) and then with 0.5% SSC containing 0.5% SDS (2×,30 min.). The envelope probe used in this initial Southern blot analysis, as well as further screening described hereinbelow, was the 1,277 bp EcoRI-Cla I fragment derived from pPAM3.

In panels A and B of FIG. 2, lane 1 corresponds to digestion of DNA with NheI, lane 2 with NheI and Hind III, lane 3 with NheI and SalI, and lane 4 with NheI and SphI. The blot in Panel A was probed with the POL fragment indicated in Panel C, and that in Panel B was probed with the ENV fragment. Panel C also shows a map of restriction sites in the predicted V/H recombinant.

All of the anticipated fragments were present in a series of single and double digestions, but, in addition, a 2.7 kb fragment not predicted from the map was present in DNA doubly digested with Nhe I and Hind III. In the Nhe I-Sal I double digest, a fragment identical in size to that seen in the Nhe I digest was observed, but this reflects partial methylation of the Sal I site with resulting inhibition of cutting. Of relevance to the cloning strategy is the fact that a proviral sequences that annealed to probes derived from pol and env sequences when digested with Nhe I were 8.3 kb in length as predicted from the map of the V/H recombinant (FIG. 2).

Cloning of Proviral Genomes from Virus Present in Monkey Serum

Figure 3:
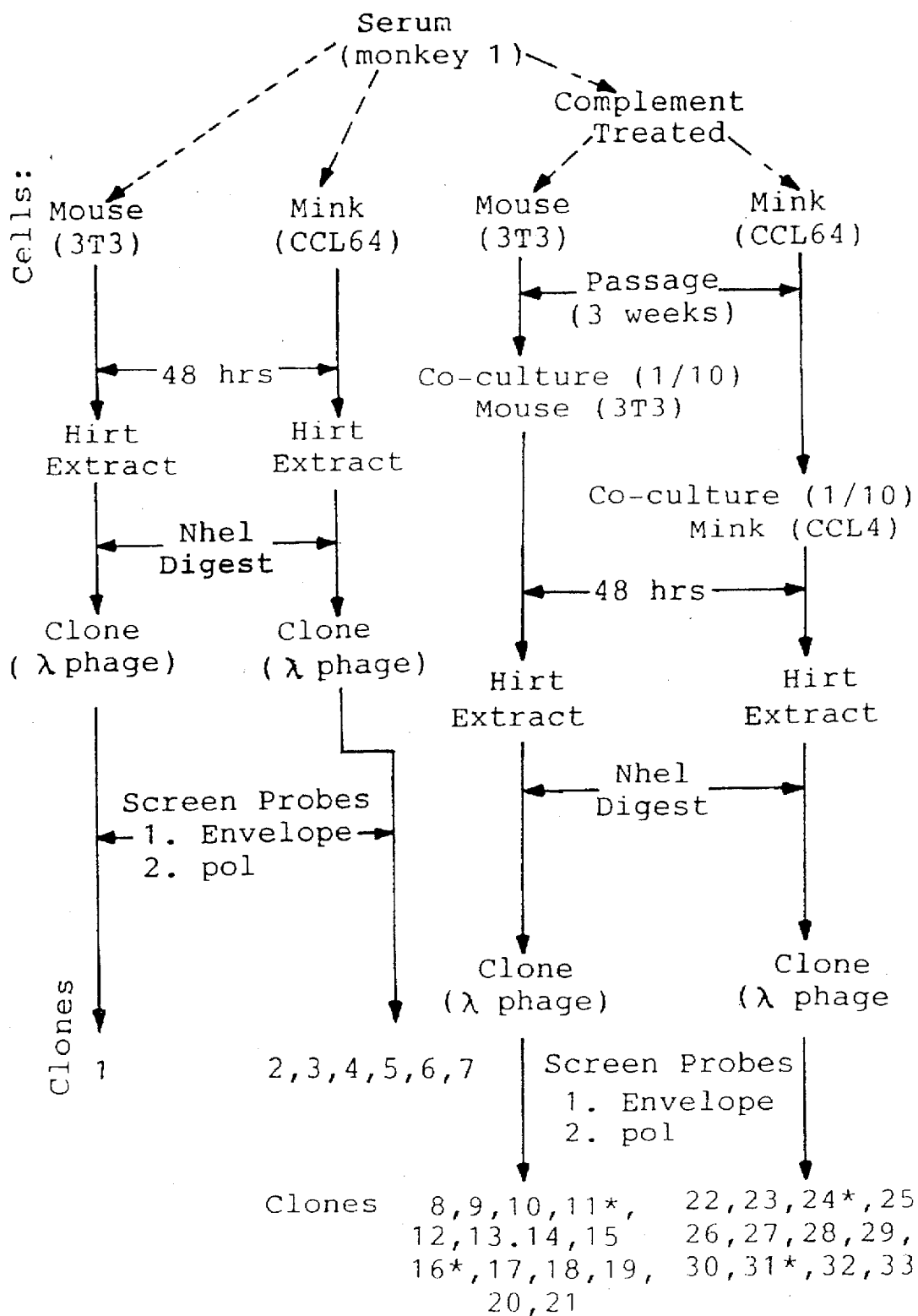
FIG. 3 is a schematic of the cloning steps for cloning of proviral genomes from virus present in the serum of a monkey having a tumor.

Serum from the monkey having the tumor hereinabove described (said monkey sometimes hereinafter referred to as monkey 1)was diluted 1:10 with human plasma, incubated for one hour at 37° C. and then used to infect mouse 3T3 and mink CCL64 cells in an effort to amplify amphotrophic, xenotropic, and MCF type viruses, if present. The serum contained $10^5$ infectious viral particles per ml. Hirt DNA (Hirt, *J. Mol. Biol.*, Vol. 26, pgs. 365–369 (1967)) was isolated from infected murine 3T3 or mink CCL64 cells, digested with Nhe I, ligated to λZAPII XbaI arms and packaged using Gigapack II Gold λ packaging extracts (Stratagene Instruction Manual Catalog No. 200216). The libraries were screened with the ENV probe (FIG. 3) and the purified clones were probed with the POL fragment. As shown in FIG. 3, the steps in the cloning procedure are indicated together with the relevant time intervals. The clones which were isolated in the experiments are numbered consecutively. Clones indicated by asterisks gave restriction enzyme fragments that deviated from those predicted for the V/H recombinant shown in FIG. 1. The Bluescript SK phagemids were rescued from each of the purified λZAPII clones as described in the Stratagene Instruction Manual Catalog No. 200216.

In another experiment, serum from monkey 1 was diluted 1:10 with human plasma, incubated for one hour at 37° C., and then used to infect 3T3 and CCL64 cells. Because the titer of virus was reduced to 1% of the initial titer by this complement treatment, the cells initially infected with the complement treated serum were cultured for 14 days in order to expand any remaining replication competent retrovirus. The cells then were co-cultured with naive cells for 48 hours and DNA was isolated by Hirt extraction for molecular cloning as hereinabove described.

The above cloning procedures, described hereinabove and shown schematically in FIG. 3, resulted in the formation of four libraries. A total of 34 vector phage clones were isolated from these four libraries with the ENV probe, and 33 of these were found to hybridize to the POL probe.

Figure 4:
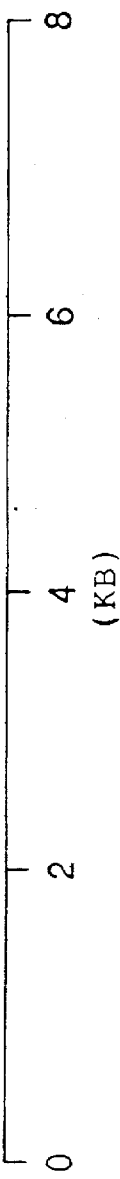
FIG. 4 (Maps A–E) depicts restriction enzyme maps of different types of cloned proviral genomes.

The Bluescript phagemid containing the inserted retroviral sequences was excised from each of the 33 clones and analyzed by digestion with HindIII, SalI, and SstI. 29 of the 33 clones had the restriction enzyme patterns A or B as shown in FIG. 4. Clone 24 had restriction pattern C as shown in FIG. 4. This restriction pattern was approximately the same size as the V/H recombinant, but the HindIII site in the ENV gene was not present and a new SstII site was observed in this same region. Clones 11 and 33 had restriction pattern D (FIG. 4). A 2,039 bp deletion beginning immediately 3' to the 5' LTR and extending into the GAG gene was identified by sequencing of clone 31. Clone 16 had restriction pattern E (FIG. 4). It contained approximately 200 bp of extraneous DNA added as an NheI fragment to the 3' end of the V/H genome during molecular cloning.

Sequence of the Envelope Coding Region of Cloned Proviruses

The envelope coding region of eleven clones (1, 2, 4, 9, 13, 16, 23, 25, 26, 27, and 31) were sequenced. Sequencing was done using the Taq Dideoxy Termination Cycle Sequencing kit and protocol from Applied Biosystems (Part No. 90/497). The reactions were analyzed using an Applied Biosystems 373A DNA Sequencer. Oligonucleotide primers were synthesized on an Applied Biosystems DNA Synthesizer 380B using phosphoramidite chemistry. Before use, the oligonucleotides were purified by Sephadex G-25 chromatography (Pharmacia NAP-25 columns).

Eight clones were identical to the predicted sequence of the V/H recombinant (McLachlin, et al., *Prog. Nucl. Acid. Res. Mol. Biol.*, Vol. 38, pgs. 91–135 (1990)). Clone 9 had a 6 bp deletion and a 3 bp substitution flanking this deletion and another single nucleotide substitution upstream from the deletion. As a result of these mutations, amino acids 100 and 168 of the ENV genes were changed, and amino acids 166 and 167 deleted. Clone 16 had an insertion of a thymine residue between codons 100 and 101 of the ENV gene forming a termination codoin(TAG) at the site of insertion and non-conservative substitutions at codons 15 and 295. Clone 25 had five non-conservative substitutions at codons 81, 100, 102, 295, and 629.

Characterization of Clone 24

Clone 24 was sequenced in its entirety. Sequencing was done as hereinabove described. The 3' end of the POL gene and the 5' two-thirds of the ENV gene diverged significantly from the sequence of the V/H recombinant (FIG. 5A). 1,536 bp of the V/H genome were replaced with 1,456 bp of extraneous sequence. The reading frames of both the POL and the ENV genes were preserved in this novel proviral genome. Comparison of the ENV gene of clone 24 with previously published ENV gene sequences indicated that the majority of the divergent region was most highly homologous to the Friend FrNx strain MCF ENV gene. (Adachi, et al., *J. Virol.*, Vol. 50, pgs. 813–821 (1984).) The alignment of the ENV sequences from clone 24, (SEQ ID NO:8) the FrNx strain MCF (SEQ ID NO:7) and the V/H recombinant (SEQ ID NO:9) (FIG. 5A) indicated that a central segment of 160 bp of clone 24 ENV sequence had relatively low homology to either the FrNx strain MCF or the V/H recombinant. Thus, the ENV gene of clone 24 was divided into three segments and each segment was compared to previously sequenced ENV genes. From nucleotide 1 to nucleotide 1049, the clone 24 ENV gene is more homologous to the Friend FrNx strain MCF (99.9%) than to any of the other sequences. From nucleotide 1050 to nucleotide 1209, the sequence of the clone 24 ENV gene had a greater degree of homology with the NZB-9-1 xenotropic murine leukemia ENV sequence (O'Neill, et al., *J. Virol.*, Vol. 53, pgs. 100–106 (1985)) than with other ENV sequences. For the remainder of the ENV gene (from nucleotide 1210 to nucleotide 1911), the sequence of clone 24 is identical to the analogous region of the V/H recombinant. The homology, at the nucleotide level, between clone 24 and the V/H recombinant, excluding the LTR's, was 99.8% 5' to the divergent region and 100% 3' to it. As shown in FIG. 5A, the numbering depicts the nucleotides from the ENV translational initiation codon. The two vertical arrows delineate the region of the clone 24 ENV gene between nucleotides 1050 and 1209 that is more homologous to the N2B-9-1 ENV sequences than either to those of Fr-Nx or the V/H recombinant. The underlined sequence indicates the segment of the ENV gene that encodes p15E.

Homologies of the various nucleotide regions of the ENV sequence of Clone 24 with the envelope coding sequences of various types of murine retrovirus types of murine retroviruses are given in Table I below. As shows in Table I, the values shown are the percentages of nucleotides in the segment of the Clone 24 env sequences that are identical to the compared sequences. Shown in parentheses are the number of gaps introduced as a result of the criteria used for the homology search. The homology search was done by employing the DNA Star computer program (DNA Star, Madison, Wis.).

TABLE I

| VIRUS TYPE | VIRUS | NUCLEOTIDE POSITION Homology (%) | | |
|---|---|---|---|---|
| | | 1–1049 | 1050–1209 | 1210–1911 |
| MCF | Friend MCF-FrNX strain | 99.1(–) | 77.0(–) | 78.6(–) |
| | Friend MCF-N.I.H. Leukemic Swiss Mice | 97.3(–) | 97.5(–) | 80.6(–) |
| | Moloney MCF-isolate 81 | 96.2(–) | 80.0(–) | 81.5(–) |
| | Friend MCF-Eveline | 95.3(–) | 76.4(–) | 69.7(–) |
| | MCF-MuLV-CI-3 isolate | 96.0(1) | 91.3(–) | 76.5(–) |
| | MCF-247 | 95.0(–) | 81.4(–) | 74.6(–) |
| | Rauscher MCF | 92.2(2) | 78.3(–) | 79.1(–) |
| XENOTROPIC | NZB-9-1 Murine Leukemia Virus | 91.5(2) | 98.8(–) | 76.4(–) |
| | CWM Murine Leukemia Virus | 91.7(2) | 96.3(–) | 76.4(–) |
| AMPHOTROPHIC | 10A1 Murine Leukemia Virus | 79.1(6) | 72.7(–) | 96.0(–) |
| | 4070A Murine Leukemia Virus | 72.2(14) | 74.5(–) | 98.7(–) |

TABLE I-continued

| VIRUS TYPE | VIRUS | NUCLEOTIDE POSITION Homology (%) | | |
|---|---|---|---|---|
| | | 1–1049 | 1050–1209 | 1210–1911 |
| ECOTROPIC | Moloney Murine Leukemia Virus | 66.4(15) | 79.5(−) | 81.5(−) |
| | AKV Murine Leukemia Virus | 58.6(15) | 80.8(−) | 75.6(−) |

Figure 5B:
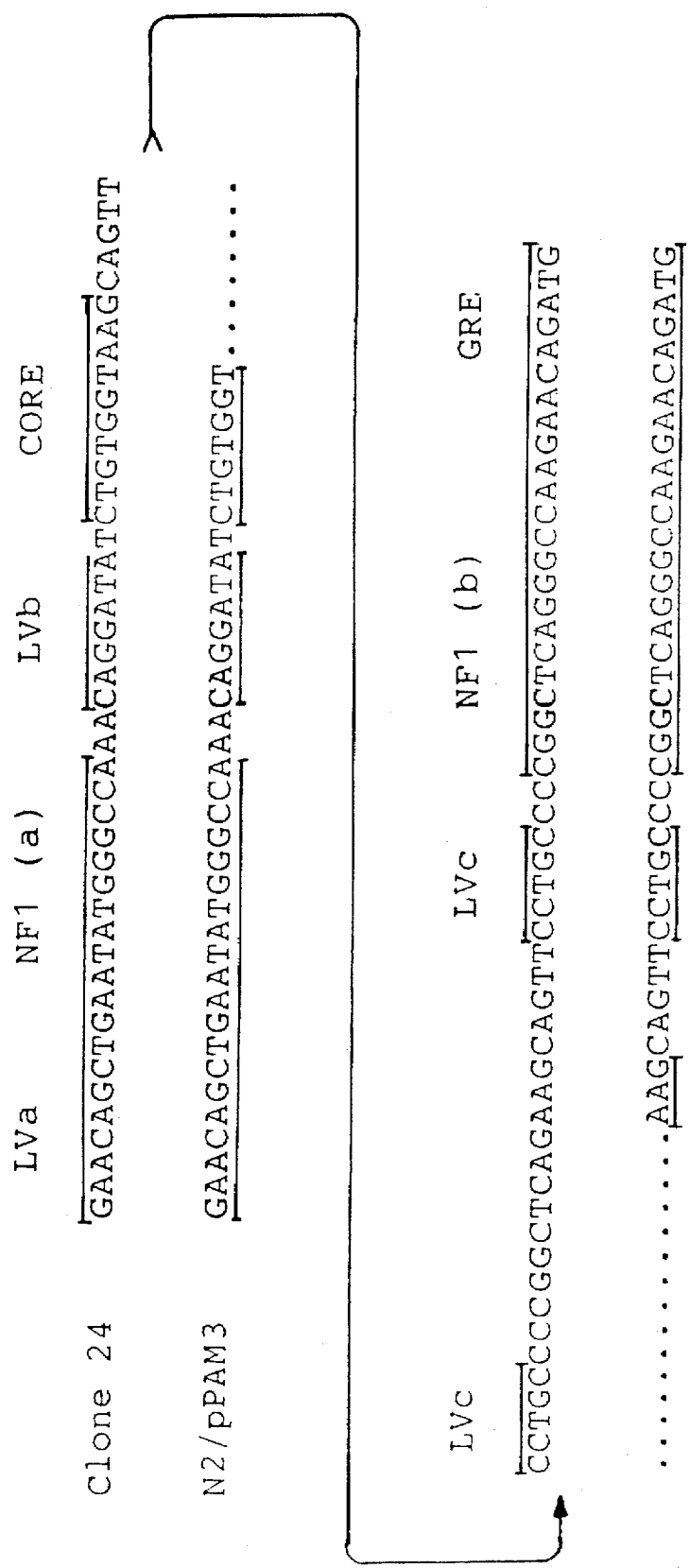
FIG. 5B is the sequence of a segment of the U3 region of the LTRs of the virus isolated from clone 24 and of the N2/pPAM3 recombinant.
Figure 14:
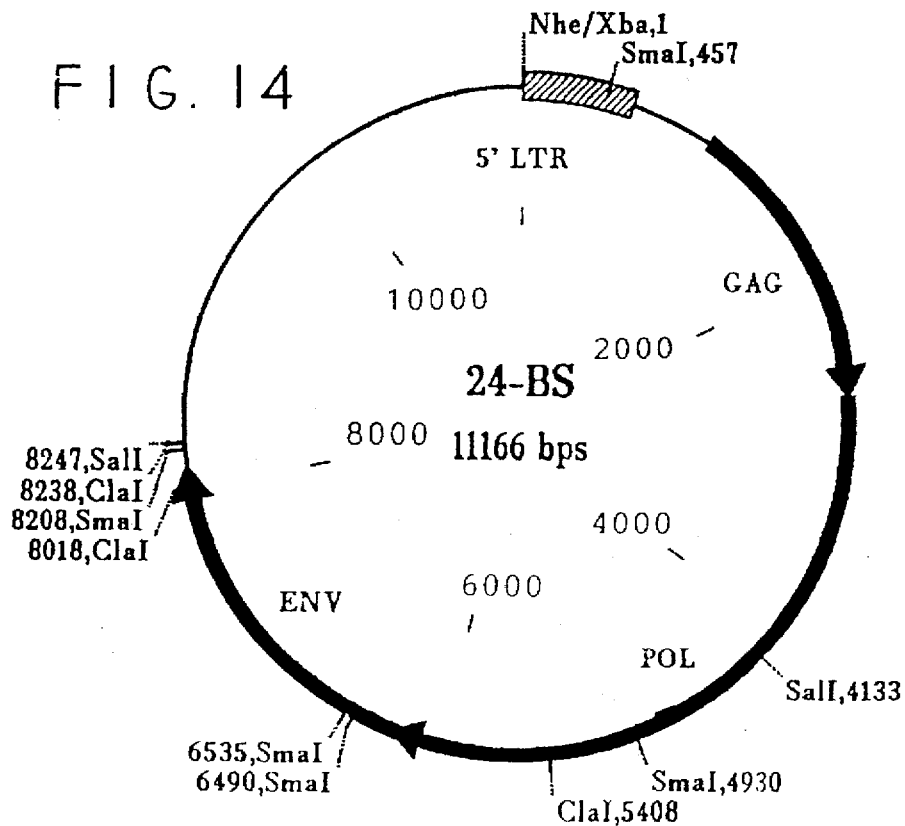
FIG. 14 is a map of plasmid p24-BS.

The U3 segment of the LTR of clone 24 has a 23 bp insertion compared to the sequence of the V/H recombinant (FIG. 5B); this insertion is within the 5' member of the two 75 bp direct repeats which comprise the enhancer region of U3 (Speck, et al., *Mol. Cell. Biol.*, Vol. 7, pgs 1101–1110 (1987); Speck, et al., *J. Virol.*, Vol. 64, pgs. 543–550 (1990)). As shown in FIG. 5B, sequences corresponding to binding sites to transcription factors are overlined or underlined. As shown in FIG. 5B, GRE is the glucocorticoid response element; LVa, LVb, and LVc correspond to binding sites for leukemia factors a, b, and c, respectively; NF-1 is nuclear factor 1; and CORE is a binding motif found in the SV40 enhancer. (Speck, et al., *Mol. Cell. Biol.*, Vol. 7, pgs. 1101–1110 (1987)). The inserted segment is a direct copy of the 23 bp 3' to it. The LTR has been sequenced in the entirety by di-deoxy terminator cycle DNA sequencing, and the sequence (SEQ ID NO:12) is shown in FIG. 5C. The novel virus potentially encoded by clone 24 was designated as the AMP/MCF virus. As stated hereinabove, the entire sequence of this virus has been determined in its entirety by di-deoxy terminator cycle DNA sequencing as hereinabove described, and the sequence is shown in FIG. 5D. A plasmid clone also was obtained and designated p24-BS. (FIG. 14.) p24-BS has been deposited with the American Type Culture Collection and has been assigned ATCC Accession No. 75847, deposited on Jun. 10, 1994.

Occurrence and Formation of AMP/MCF (Clone 24) Virus

PCR analysis of DNA samples from monkey 1 as well as two other monkeys (hereinafter referred to as monkeys 2 and 3) that developed lymphoma was undertaken as follows.

Previously described primers (Bodine, et al., *Proc. Nat. Acad. Sci.*, Vol. 85, pgs. 5404–5408 (1988)) were used to amplify a 227 bp fragment in the amphotropic envelope. The primers used to assay for AMP/MCF, MCF, and xenotropic envelope sequence in genomic DNA and the size of the amplified fragment are listed below:

| Envelope | PCR Oligonucleotides | Size |
|---|---|---|
| AMP/MCF | 5': ATGATTCCTCAGTGGTCTCCAGTG (SEQ ID NO: 5) 3': TTCGTTGAGGTCTGTCTGGATAGC (SEQ ID NO: 6) | 979 bp |
| MCF | 5': GGACTYGGGTGTCGCACTCCC (SEQ ID NO: 1) 3': ACTGGAGACCRCTGAGGAATC (SEQ ID NO: 2) | 245 bp |
| Xenotropic | 5': GGATGACCCAGAACCCGATATTGG (SEQ ID NO: 3) 3': ATCATAACAGGGGCCCTGATCCTT (SEQ ID NO: 4) | 249 bp |

In the MCF primer sequences, Y is a pyrimidine, and R is a purine.

The primers used for the AMP/MCF envelope were determined using PRIMER 2 (a primer designer program from Scientific and Educational Software, State Line, Pa.). The MCF and xenotropic specific primers were designed by first aligning all the previously sequenced MCF or xenotropic ENV genes and subsequently choosing sequences which were in conserved regions in each class.

Figure 6:
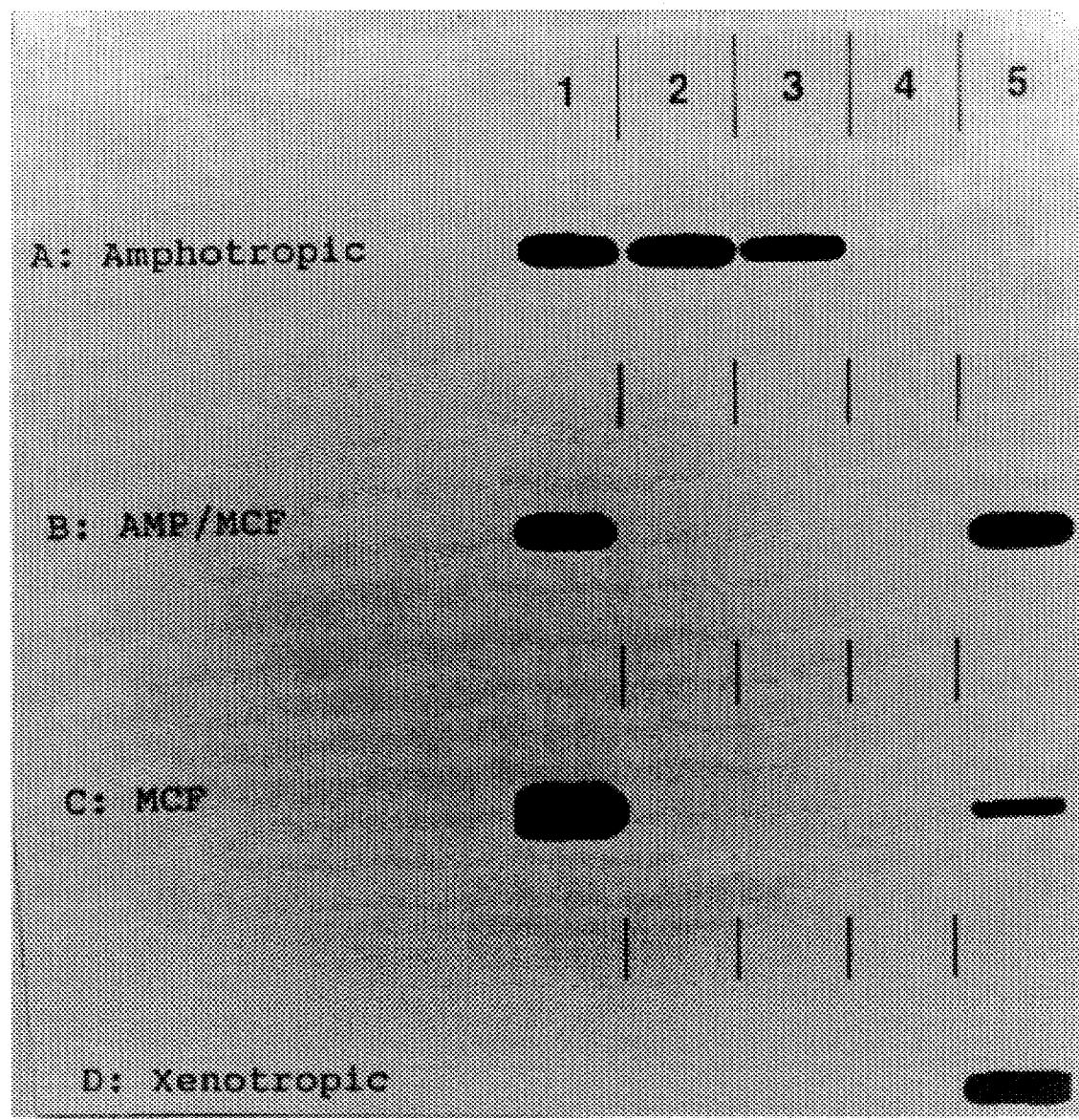
FIGS. 6A, 6B, 6C, and 6D are results of PCR analysis of tumor DNA for amphotropic, AMP/MCF, MCF, or xenotropic envelope specific sequences.

The conditions used for PCR were 94° C. for 1 minute (denaturation), 65° C. for 1 minute (annealing), and 72° C. for 1.5 minutes (elongation) for a total of 25 cycles. Genomic DNA (400 mg) was used as a template and 0.1 µl of [$^{32}$P] dCTP (3,000 Ci/mole) (Amersham Corp.) was added in a total volume of 100 µl. The above PCR procedure also was performed on a negative control monkey DNA and a positive control. As shown in FIG. 6, lane 1 is the PCR blot resulting from the analysis of the DNA of monkey 1; lane 2 is the PCR blot resulting from the analysis of the DNA of monkey 2; lane 3 is the PCR blot resulting from the analysis of the DNA of monkey 3; lane 4 is the PCR blot of the analysis of the negative control monkey DNA; and lane 5 is the PCR blot of the analysis of the positive control. Positive control DNA's were recovered from mink CC64 cells infected with amphotropic 4070A virus, MCF virus 247, xenotropic virus N2B-9-1, or from monkey serum (AMP/MCF).

As demonstrated previously (Donahue, et al., *J. Exp. Med.*, Vol. 176, pgs. 1125–1135 (1992)), amphotropic envelope sequences were present in DNA from monkeys 1, 2, and 3 (FIG. 6A) Primers that span the 3' recombination junction and therefore are specific for the AMP/MCF ENV gene were devised. An amplified fragment of expected size was present on analysis of thymic DNA from monkey 1, but no such product was detected in DNA samples from monkeys 2 and 3 (FIG. 6B).

DNA from monkeys 1, 2, and 3 also was analyzed with primer pairs specific for MCF and xenotropic ENV sequences. These primers are homologous to conserved segments of these genes that differ among the various classes of ENV genes (O'Neill, et al., *J. Virol.*, Vol. 58, pgs. 359–366 (1986)). An amplified product with the MCF primers was seen with template DNA from monkey 1, presumably derived from the AMP/MCF genome (FIG. 6C) but no other amplified products were observed (FIGS. 6C and 6D). Southern analysis using both MCF and xenotropic ENV specific probes (O'Neill, et al., 1986) confirmed the PCR results. Specific bands were seen with the MCF probe on analysis of DNA from monkey 1 but not with DNA from monkeys 2 and 3.

The numbers of integrated copies of the AMP/MCF and V/H recombinant proviruses was determined by both "integration site" analysis (FIG. 7) and quantitative genomic Southern blots (data not shown) using probes which are specific for the MCF or amphotropic envelope coding sequences. In the "integration site" analysis, the genomic DNA was digested with a restriction enzyme which has a single site in proviral DNA yielding a unique band for each integration position. Multiple hybridizing fragments were seen with the amphotropic ENV probe on BglII digested thymic DNA of monkey 1 and monkey 2 (FIG. 7A) consistent with a large number of integrated proviral copies.

Genomic DNA from monkey 1, which was digested with BamHI, BglI, BglII, Hind III, or SphI (blots of which are shown in lanes 1 through 5, respectively, of FIG. 7B) was probed with an MCF specific probe. (O'Neill, et al., *J. Virol.*, Vol. 58, pgs. 359–366 (1986)). With the MCF specific probe, 11–12 bands were seen on analysis of genomic DNA from monkey 1 (FIG. 7B).

For quantitative genomic Southern analysis, specific amounts (corresponding to variable copy equivalents) of plasmid DNA containing the appropriate ENV genes (clone 24 for AMP/MCF and clone 25 for the V/H recombinant) were added to a specific amount of control monkey DNA. The signal intensity obtained on analysis of DNA from monkeys 1 and 2 was compared to standards using a phosphoimager for quantitative analysis.

Tumor DNA from monkey 1 contained an estimated 12 copies of the AMP/MCF proviral genome and about 25 copies of the V/H genome. DNA from monkey 2 contained 14 integrated copies per genome of the V/H recombinant provirus.

Figure 8A:
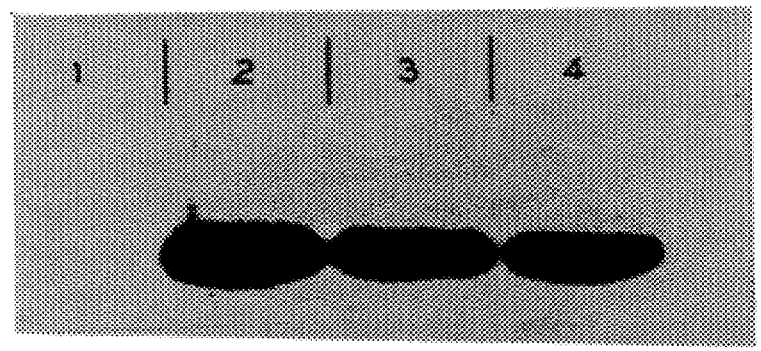
FIGS. 8A and 8B depict blots of DNA's probed with primers specific for AMP/MCF env gene sequences.

The AMP/MCF virus arose during passage of the A2 producer line. DNA was isolated from cells in culture at 2, 19, 22, 25 and 33 months after isolation of the clone. Templated DNAs were amplified with primers specific for the AMP/MCF ENV sequences. As shown in FIG. 8A, the template DNAs were as follows: lane 1-negative control DNA from CCL64 cells; lanes 2 and 3-DNA from CCL64 cells exposed to serum from monkey 1 or medium conditioned by the A2 producer clone, respectively; lane 4-DNA from the thymus of monkey 1. Further template DNAs shown in FIG. 8B were as follows: lane 1-DNA from NIH 3T3 cells; lane 2-DNA from an original low titer producer line, N273 (Bodine, et al, 1990); lanes 3–7-DNA derived from high titer A2 (Bodine, et al., 1990) producer line at 2, 19, 22, 25 or 33 months after the initial isolation, respectively.

Figure 8B:
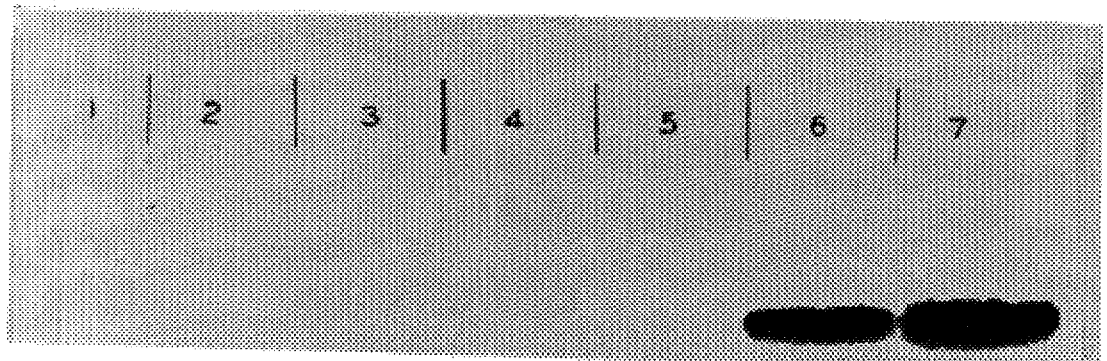

The specific product amplified with the AMP/MCF primer pair was first detected in the DNA from the cells at 25 months and was of greater intensity when the DNA was analyzed from the passage at 33 months. Culture medium from A2 cells after the 33 month passage transferred the AMP/MCF viral genome into mink cells (FIG. 8B).

Example 2

Construction of Plasmid Vector Including the AMP/MCF LTR

As stated in Example 1, the AMP/MCF replication competent retrovirus contains a 23 bp insert within the enhancer region of the LTR promoter. This example describes the construction of a retroviral plasmid vector containing an LTR having this 23 bp insert.

Figure 11:
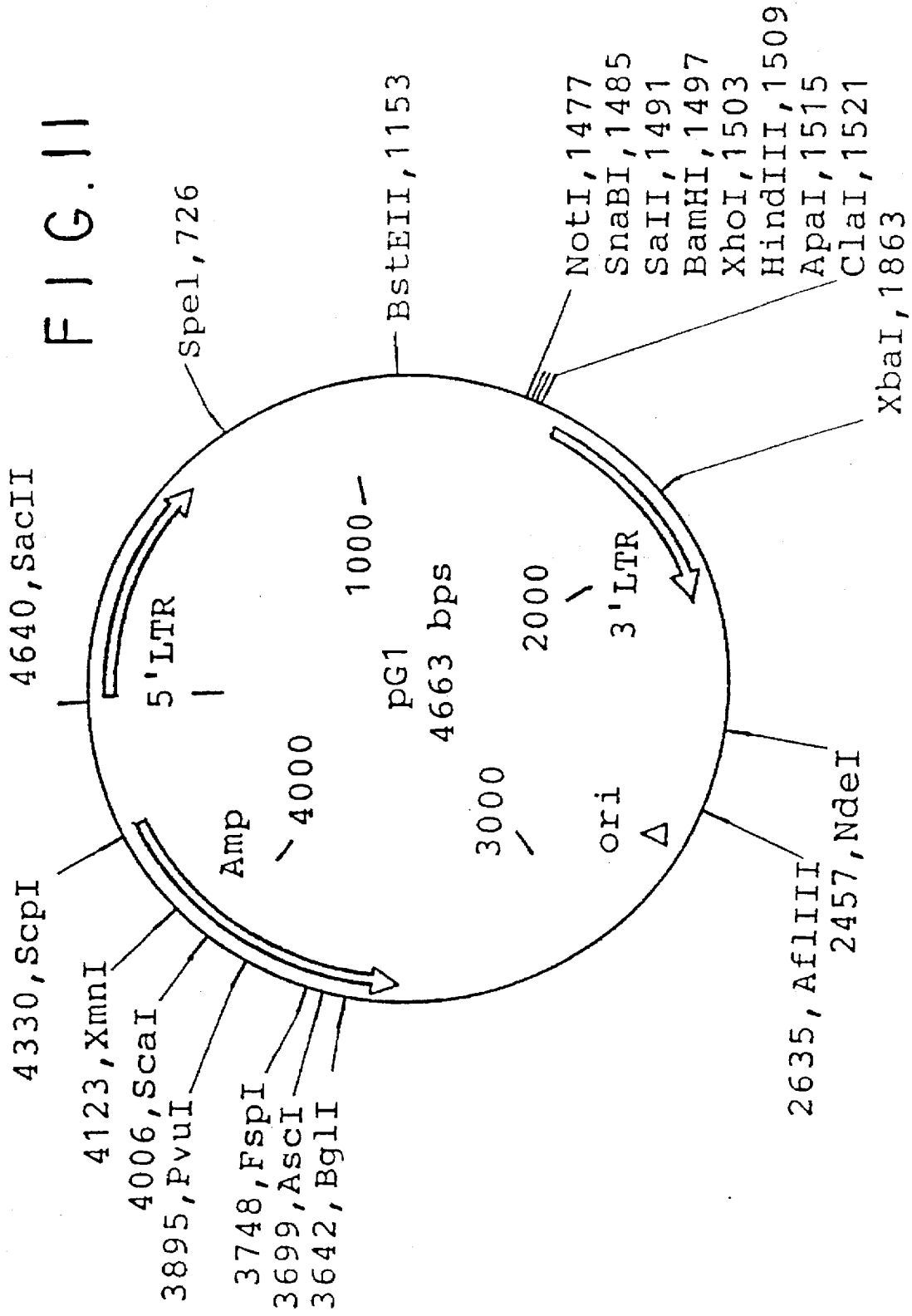
FIG. 11 is a map of plasmid pG1.

Plasmid pG1 was constructed from pLNSX (Palmer et al., Blood, 73:438–445; 1989). The construction strategy for plasmid pG1 is shown in FIG. 9. The 1.6 kb EcoRI fragment, containing the 5' Moloney Sarcoma Virus (MoMuSV) LTR, and the 3.0 kb EcoRI/ClaI fragment, containing the 3' LTR, the bacterial origin of replication and the ampicillin resistance gene, were isolated separately. A linker containing seven unique cloning sites was then used to close the EcoRI/ClaI fragment on itself, thus generating the plasmid pGO. The plasmid pGO was used to generate the vector plasmid pG1 by the insertion of the 1.6 kb EcoRI fragment containing the 5' LTR into the unique EcoRI site of pGO. Thus, pG1 (FIG. 11) consists of a retroviral vector backbone composed of a 5' portion derived from MoMuSV, a short portion of gag in which the authentic ATG start codon has been mutated to TAG (Bender et al., *J. Virol.*, Vol. 61, pgs. 1639–1649 (1987)), a 54 base pair multiple cloning site (MCS) containing from 5' to 3' the sites EcoRI, NotI, SnaBI, SalI, BamHI, XhoI, HindIII, ApaI, and ClaI, and a 3' portion of MoMuLV from base pairs 7764 to 7813 numbered as described in Van Beveren et al., *Cold Spring Harbor*, Vol. 2, pg. 567, (1985). (FIG. 10). The MCS was designed to generate a maximum number of unique insertion sites, based on a screen of non-cutting restriction enzymes of the pG1 plasmid, the neo$^R$ gene, the β-galactosidase gene, the hygromycin$^R$ gene, and the SV40 promoter.

Figure 12:
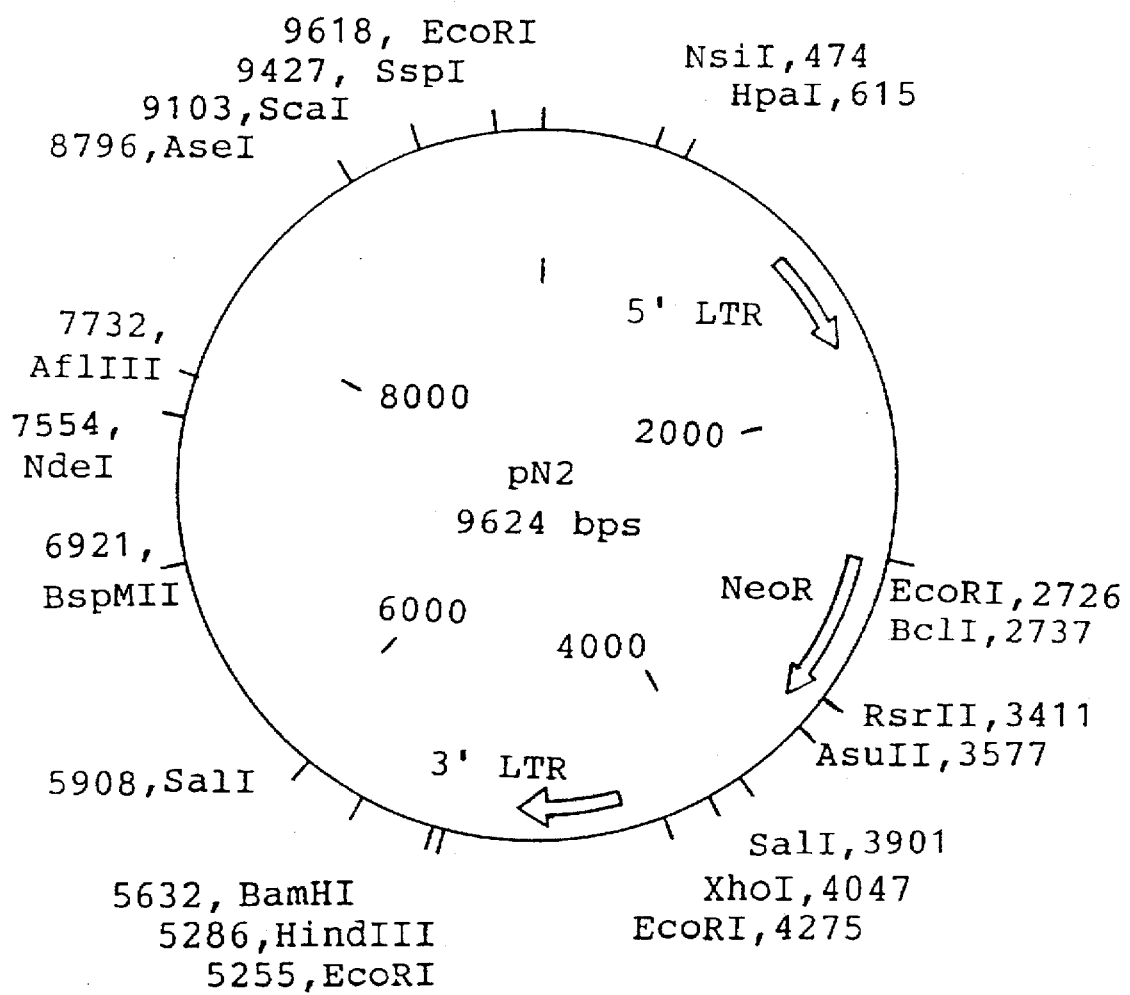
FIG. 12 is a map of plasmid pN2.
Figure 13:
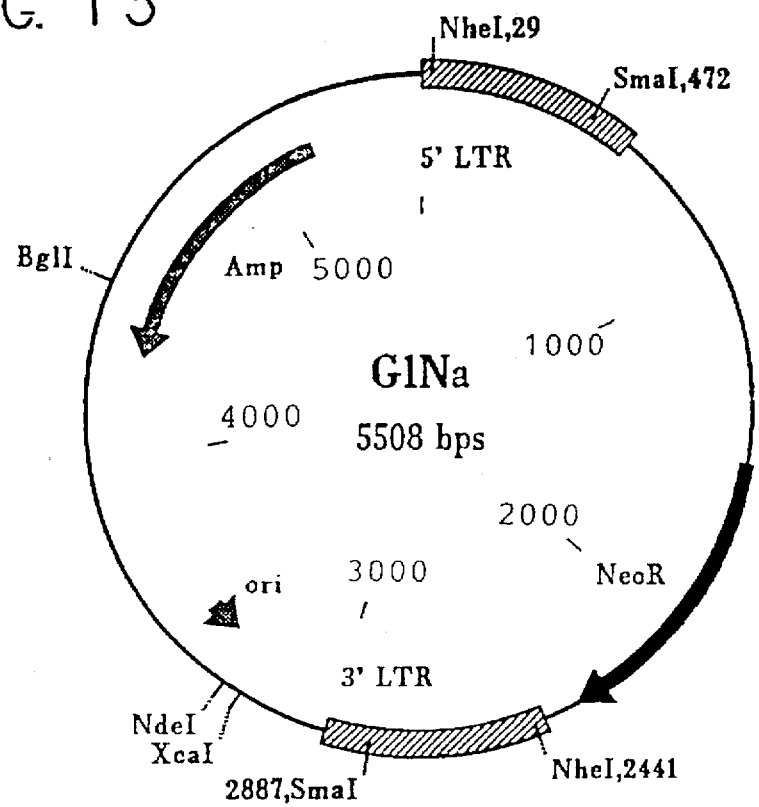
FIG. 13 is a map of plasmid pG1Na.

The "backbone" vector pG1Na was constructed from pG1 and pN2 (Armentano, et al., *J. Virology*, Vol. 61, pgs. 1647–1650 (1987)). pG1Na was constructed by cutting pN2 (FIG. 12) with EcoRI and AsuII, filling in the ends of the EcoRI/AsuII fragment containing the neo$^R$ gene, and ligating the fragment into SnaBI digested pG1 to form pG1Na (FIG. 13).

The 23 bp insertion in the LTR of the AMP/MCF virus is within the U3 region of the LTR. In Moloney Murine Leukemia Virus derived retroviral plasmid vectors, this region is flanked by an NheI site at the extreme 5' end and an SmaI site within the r region of the LTR.

During the isolation and cloning of the AMP/MCF virus (Clone 24) as described in Example 1, the NheI and XbaI sites were destroyed. In order to clone a segment containing the 23 bp insertion in the LTR into a plasmid vector, the NheI/XbaI site (TCTAGC) in plasmid p24-BS (FIG. 14) is mutated back to an NheI site (GCTAGC). The AMP/MCF viral DNA then is cut with NheI and SmaI. An NheI-SmaI fragment containing the 23 bp insertion is obtained, and is cloned into NheI and SmaI digested pG1Na (FIG. 13), whereby the 3' LTR of pG1Na contains the LTR sequence found in the AMP/MCF virus.

Example 3

Figure 15:
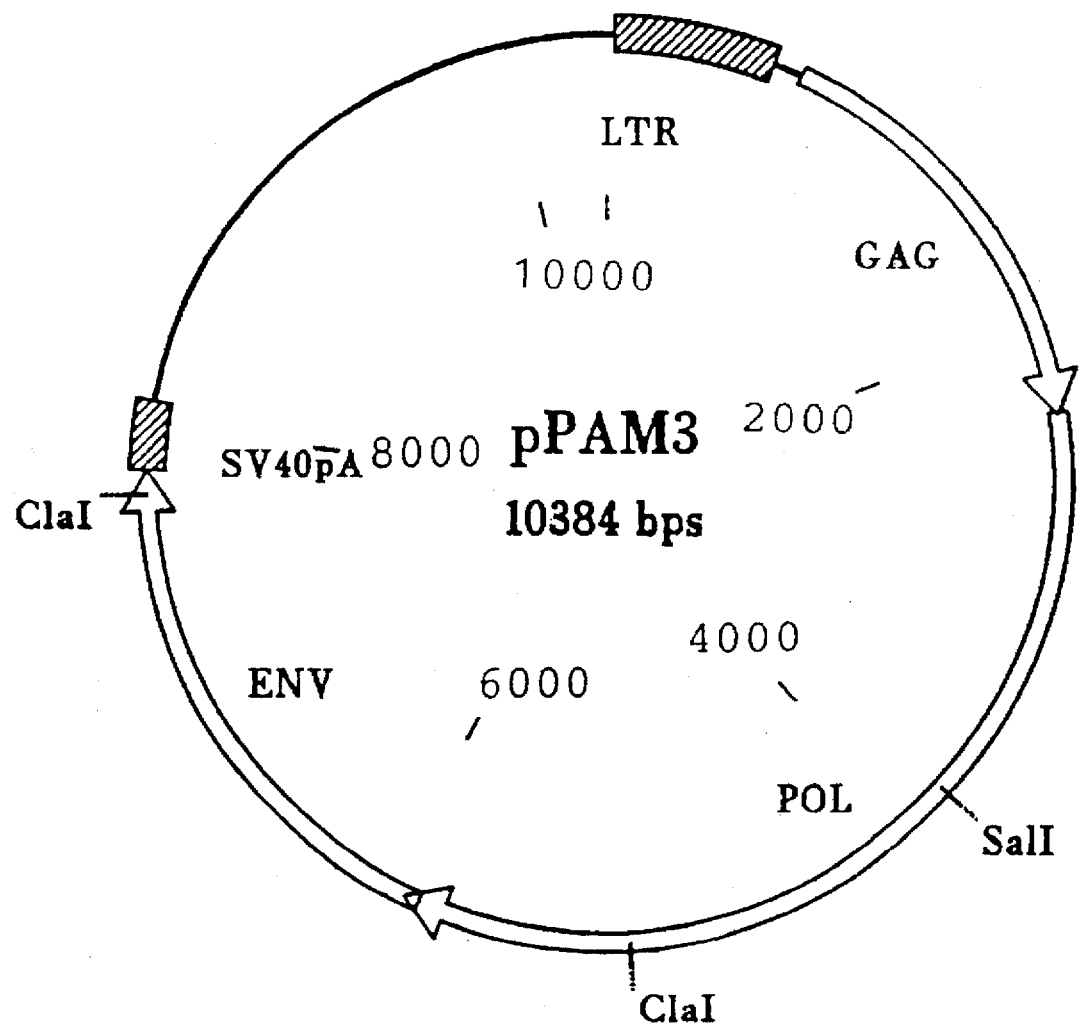
FIG. 15 is a map of plasmid pPAM3.
Figure 16:
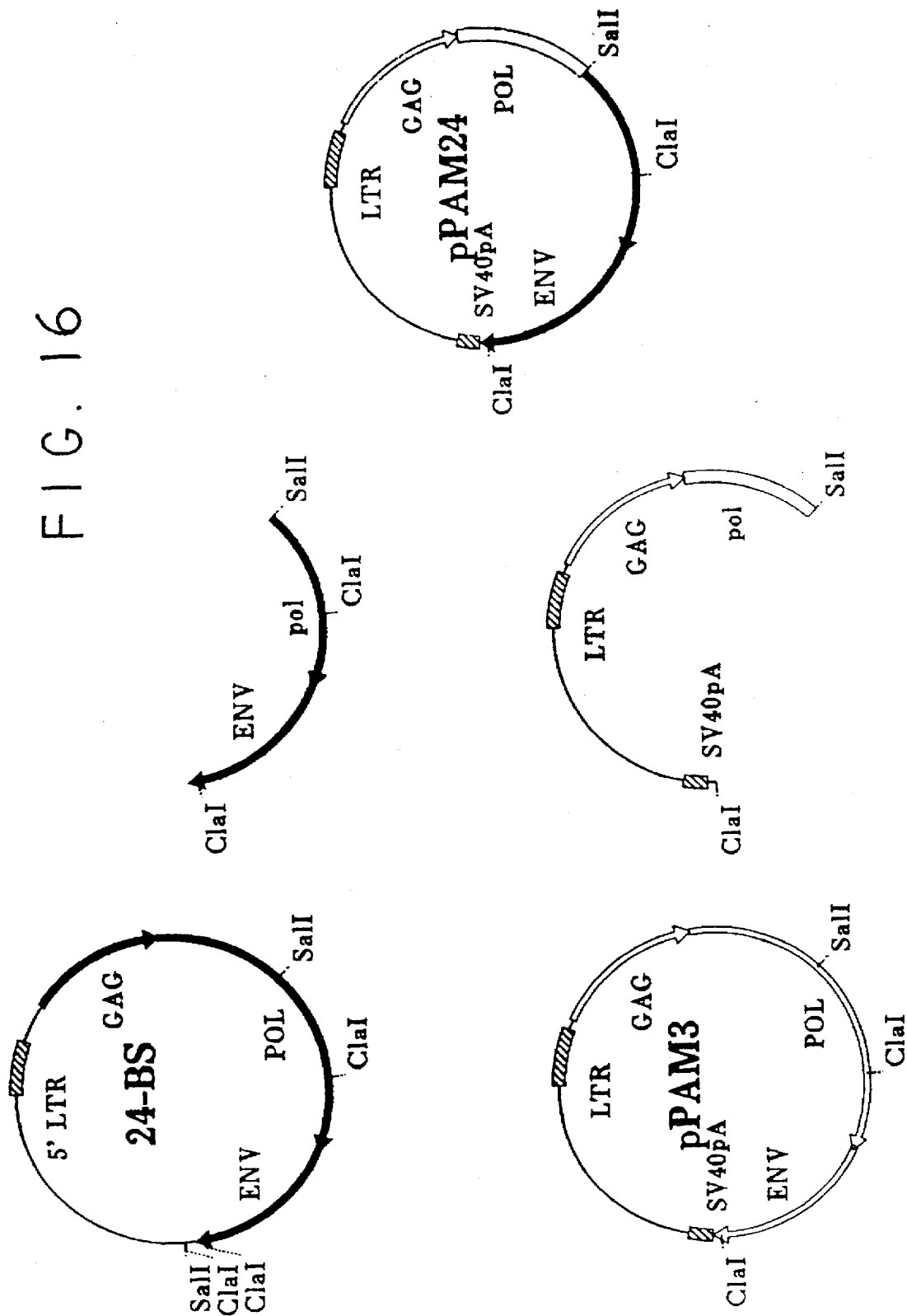
FIG. 16 is a schematic of the construction of plasmid pPAM24.

Construction of Packaging Plasmid Including the AMP/MCF Envelope p24-BS (FIG. 14) is cut with SalI and ClaI, and a fragment including the env coding region and a portion of the pol coding region is removed. pPAM3 (FIG. 15) also is cut with SalI and ClaI, and the env coding region and a portion of the pol coding region is removed. The SalI-ClaI fragment removed from p24-BS then is ligated into SalI-ClaI digested pPAM3 to form pPAM24. A schematic of the construction of pPAM24 is shown in FIG. 16. pPAM24 then is transfected into NIH 3T3 cells to form a packaging cell line.

The disclosure of all patents, publications, (including published patent applications), and database entries referenced in this specification are specifically incorporated herein by reference in their entirety to the same extent as if each such individual patent, publication, and database entry were specifically and individually indicated to be incorporated by reference.

It is to be understood, however, that the scope of the present invention is not to be limited to the specific embodiments described above. The invention may be practiced other than as particularly described and still be within the scope of the accompanying claims.

What is claimed is:

1. A retroviral vector particle including a nucleic acid sequence encoding a retroviral envelope, said nucleic acid sequence encoding said retroviral envelope having the nucleic acid sequence of (SEQ ID NO:8).

2. A producer cell transduced with the retroviral vector particle of claim 1.

3. Infectious viral particles generated from the producer cell of claim 2.

4. Eukaryotic cells transduced with the infectious viral particles of claim 3.

5. A nucleic acid sequence encoding a retroviral envelope, said nucleic acid sequence having the nucleic acid sequence of (SEQ ID NO:8).

6. A packaging cell line including the nucleic acid sequence of claim 5.

7. A nucleic acid sequence encoding a retroviral LTR, said nucleic acid sequence having the sequence of (SEQ ID NO:12).

8. A packaging cell line including the nucleic acid sequence of claim 7.

9. A retroviral vector particle including a nucleic acid sequence encoding a retroviral LTR, said nucleic acid sequence encoding said retroviral LTR having the nucleic acid sequence of (SEQ ID NO:12).

10. A producer cell transduced with the retroviral vector particle of claim 9.

11. Infectious viral particles generated from the producer cell of claim 10.

12. Eukaryotic cells transduced with the infectious viral particles of claim 11.

13. A retroviral vector particle including a first nucleic acid sequence encoding a retroviral envelope, said first nucleic acid sequence encoding said retroviral envelope having the nucleic acid sequence of (SEQ ID NO:8), and a second nucleic acid sequence encoding a retroviral LTR, said second nucleic acid sequence encoding said retroviral LTR having the nucleic acid sequence of (SEQ ID NO:12).

14. A producer cell transduced with the retroviral vector particle of claim 13.

15. Infectious viral particles generated from the producer cell of claim 14.

16. Eukaryotic cells transduced with the infectious viral particles of claim 15.

17. A retroviral packaging plasmid including a nucleic acid sequence encoding retroviral envelope, said nucleic acid sequence encoding said retrovital envelope having the nucleic acid sequence of (SEQ ID NO:8).

18. A retroviral plasmid vector including a nucleic acid sequence encoding a retroviral LTR having the nucleic acid sequence of (SEQ ID NO:12).

* * * * *

SEQUENCE LISTING ( 1 ) GENERAL INFORMATION:

( i i i ) NUMBER OF SEQUENCES: 14

( 2 ) INFORMATION FOR SEQ ID NO: 1:

( i ) SEQUENCE CHARACTERISTICS:
        ( A ) LENGTH: 21 bases
        ( B ) TYPE: nucleic acid
        ( C ) STRANDEDNESS: single
        ( D ) TOPOLOGY: linear ( i i ) MOLECULE TYPE: oligonucleotide ( i x ) FEATURE:
        ( A ) NAME/KEY: PCR primer
        ( D ) OTHER INFORMATION: Y is a pyrimidine ( x i ) SEQUENCE DESCRIPTION: SEQ ID NO: 1:

GGACTYGGGT GTCGCACTCC C                                                             21

( 2 ) INFORMATION FOR SEQ ID NO: 2:

( i ) SEQUENCE CHARACTERISTICS:
        ( A ) LENGTH: 21 bases
        ( B ) TYPE: nucleic acid
        ( C ) STRANDEDNESS: single
        ( D ) TOPOLOGY: linear ( i i ) MOLECULE TYPE: oligonucleotide ( i x ) FEATURE:
        ( A ) NAME/KEY: PCR primer
        ( D ) OTHER INFORMATION: R is a purine ( x i ) SEQUENCE DESCRIPTION: SEQ ID NO: 2:

ACTGGAGACC RCTGAGGAAT C                                                            21

( 2 ) INFORMATION FOR SEQ ID NO: 3:

( i ) SEQUENCE CHARACTERISTICS:
        ( A ) LENGTH: 24 bases
        ( B ) TYPE: nucleic acid
        ( C ) STRANDEDNESS: single
        ( D ) TOPOLOGY: linear ( i i ) MOLECULE TYPE: oligonucleotide ( i x ) FEATURE:
        ( A ) NAME/KEY: PCR primer ( x i ) SEQUENCE DESCRIPTION: SEQ ID NO: 3:

GGATGACCCA GAACCCGATA TTGG                                                       24

( 2 ) INFORMATION FOR SEQ ID NO: 4:

( i ) SEQUENCE CHARACTERISTICS:
        ( A ) LENGTH: 24 bases
        ( B ) TYPE: nucleic acid
        ( C ) STRANDEDNESS: single
        ( D ) TOPOLOGY: linear ( i i ) MOLECULE TYPE: oligonucleotide ( i x ) FEATURE:
        ( A ) NAME/KEY: PCR primer ( x i ) SEQUENCE DESCRIPTION: SEQ ID NO: 4:

ATCATAACAG GGGCCCTGAT CCTT                                                       24

( 2 ) INFORMATION FOR SEQ ID NO: 5:

( i ) SEQUENCE CHARACTERISTICS:
        ( A ) LENGTH: 24 bases
        ( B ) TYPE: nucleic acid
        ( C ) STRANDEDNESS: single
        ( D ) TOPOLOGY: linear ( i i ) MOLECULE TYPE: oligonucleotide ( i x ) FEATURE:
        ( A ) NAME/KEY: PCR primer ( x i ) SEQUENCE DESCRIPTION: SEQ ID NO: 5:

```
ATGATTCCTC AGTGGTCTCC AGTG                                          24
```

( 2 ) INFORMATION FOR SEQ ID NO: 6:

( i ) SEQUENCE CHARACTERISTICS:
        ( A ) LENGTH: 24 bases
        ( B ) TYPE: nucleic acid
        ( C ) STRANDEDNESS: single
        ( D ) TOPOLOGY: linear ( i i ) MOLECULE TYPE: oligonucleotide ( i x ) FEATURE:
        ( A ) NAME/KEY: PCR primer ( x i ) SEQUENCE DESCRIPTION: SEQ ID NO: 6:

```
TTCGTTGAGG TCTGTCTGGA TAGC                                          24
```

( 2 ) INFORMATION FOR SEQ ID NO: 7:

( i ) SEQUENCE CHARACTERISTICS:
        ( A ) LENGTH: 1914 bases
        ( B ) TYPE: nucleic acid
        ( C ) STRANDEDNESS: single
        ( D ) TOPOLOGY: linear ( i i ) MOLECULE TYPE: genomic DNA ( i x ) FEATURE:
        ( A ) NAME/KEY: MCF FrNx envelope sequence ( x i ) SEQUENCE DESCRIPTION: SEQ ID NO: 7:

```
ATGGAAGGTC CAGCGTTCTC AAAACCCCTT AAAGATAAGA TTAACCCGTG GGGCCCCCTG
ATAGTCCTGG GGATCTTAAT AAGGGCAGGA GTATCAGTAC AACATGACAG CCCTCACCAA
GTCTTCAATG TTACTTGGAG AGTTACCAAC TTAATGAGAG GACAAACAGC TAACGCTACC
TCCCTCCTGG GGACAATGAC AGATGCCTTT CCTATGCTGT ACTTCGACTT GTGCGATTTA
ATAGGGACG ATTGGGATGA GACCGGACTT GGGTGTCGCA CTCCCGGGGG AAGAAAAAGG
GCAAGAACAT TTGACTTCTA TGTTTGCCCC GGGCATACTG TACCAACAGG GTGTGGAGGG
CCGAGAGAGG GCTACTGTGG CAAATGGGGC TGTGAGACCA CTGGACAGGC ATACTGGAAG
CCATCATCAT CATGGGACCT AATTTCCCTT AAGCGAGGAA ACACCCCTCG GAATCAGGGC
CCCTGTTATG ATTCCTCAGT GGTCTCCAGT GGCATCCAAG GTGCCACACC GGGGGGTCGA
TGCAATCCCC TAGTCCTAGA ATTCACTGAC GCGGGTAAAA AGGCCAGCTG GGATGGCCCC
AAAGTATGGG GACTAAGACT GTACCGATCC ACAGGGATCG ACCCGGTGAC CCGGTTCTCT
TTGACCCGCC AGGTCCTCAA TATAGGGCCC CGCATCCCCA TTGGGCCTAA TCCCGTGATC
ACTGGCCAAC TACCCCCCTC CCGACCCGTG CAGATCAGGC TCCCCAGGCC TCCTCAGCCT
CCTCCTACAG GCGCAGCCTC TATGGTCCCT GGGACTGCCC CACCTTCTCA ACAACCTGGG
```

-continued

```
ACGGGAGACA  GGCTGCTAAA  CCTGGTAGAT  AGAGCATACC  AAGCACTCAA  CCTCACCAGT
CCTGACAAAA  CCCAAGAGTG  CTGGTTGTGT  CTGGTATCGG  GACCCCCCTA  CTACGAAGGG
GTTGCCGTCC  TAGGTACTTA  CTCCAACCAT  ACCTCTGCCC  CAGCTAACTG  CTCCGTGGCC
TCCCAACACA  AGCTGACCCT  GTCCGAAGTG  ACTGGACGGG  GACTCTGCAT  AGGAACAGTG
CCAAAAACTC  ACCAGGCCCT  GTGCAACACT  ACCCTTAAGG  CAGGCAAAGG  GTCTTACTAT
CTAGTTGCCC  CCACAGGAAC  TATGTGGGCA  TGTAACACTG  GACTCACTCC  ATGCCTATCT
GCCACCGTGC  TTAATCGCAC  CACTGACTAT  TGCGTTCTCG  TGGAATTATG  GCCCAGGGTC
ACCTACCATC  CTTCCAGTTA  CGTCTATAGC  CAGTTTGAAA  ATCCTATAG   ACATAAAGA
GAACCAGTGT  CCTTAACCTT  GGCCTTATTA  TTAGGTGGGC  TAACTATGGG  TGGCATCGCC
GCGGGAGTAG  GGACAGGAAC  TACCGCCCTG  GTCGCCACCC  AGCAGTTTCA  GCAGCTCCAT
GCTGCCGTAC  AAGATGATCT  CAAAGAAGTA  GAAAAGTCAA  TTACTAACCT  AGAAAAGTCT
CTTACTTCGT  TGTCTGAGGT  TGTACTGCAG  AATCGACGAG  GCCTAGACCT  GTTGTTCCTA
AAAGAGGGAG  GACTGTGTGC  TGCCCTAAAA  GAAGAATGTT  GTTTCTATGC  TGACCATACA
GGCCTAGTAA  GAGATAGTAT  GGCCAAATTA  AGAGAGAGAC  TCTCTCAGAG  ACAAAAACTA
TTTGAGTCGA  GCCAAGGATG  GTTCGAAGGA  TGGTTTAACA  GATCCCCTG   GTTTACCACG
TTGATATCCA  CCATCATGGG  GCCTCTCATT  ATACTCCTAC  TAATTCTGCT  TTTTGGACCC
TGCATTCTTA  ATCGATTAGT  TCAATTTGTT  AAAGACAGGA  TCTCAGTAGT  CCAGGCTTTA
GTCCTGACTC  AACAATACCA  CCAGCTAAAA  CCACTAGAAT  ACGAGCCACA  ATAA
```

( 2 ) INFORMATION FOR SEQ ID NO: 8:

( i ) SEQUENCE CHARACTERISTICS:
        ( A ) LENGTH: 1911 bases
        ( B ) TYPE: nucleic acid
        ( C ) STRANDEDNESS: single
        ( D ) TOPOLOGY: linear ( i i ) MOLECULE TYPE: genomic DNA ( i x ) FEATURE:
        ( A ) NAME/KEY: retroviral envelope sequence ( x i ) SEQUENCE DESCRIPTION: SEQ ID NO: 8:

```
ATGGAAGGTC  CAGCGTTCTC  AAAACCCCTT  AAAGATAAGA  TTAACCCGTG  GGGCCCCCTG
ATAGTCCTGG  GGATCTTAAT  AAGGGCAGGA  GTATCAGTAC  AACATGACAG  CCCTCACCAG
GTCTTCAATG  TTACTTGGAG  AGTTACCAAC  TTAATGAGAG  GACAAACAGC  TAACGCTACC
TCCCTCCTGG  GGACAATGAC  AGATGCCTTT  CCTATGCTGT  ACTTCGACTT  GTGCGATTTA
ATAGGGGACG  ATTGGGATGA  GACTGGACTT  GGGTGTCGCA  CTCCCGGGGG  AAGAAAACGG
GCAAGAACAT  TTGACTTCTA  TGTTTGCCCC  GGGCATACTG  TACCAACAGG  GTGTGGAGGG
CCGAGAGAGG  GCTACTGTGG  CAAATGGGGC  TGTGAGACCA  CTGGACAGGC  ATACTGGAAG
CCATCATCAT  CATGGGACCT  AATTTCCCTT  AAGCGAGGAA  ACACCCCTCG  GAATCAGGGC
CCCTGTTATG  ATTCCTCAGT  GGTCTCCAGT  GGCATCCAGG  GTGCCACACC  GGGGGGTCGA
TGCAATCCCC  TAGTCCTAGA  ATTCACTGAC  GCGGGTAAAA  AGGCCAGCTG  GGATGGCCCC
AAAGTATGGG  GACTAAGACT  GTACCAATCC  ACAGGGATCG  ACCCGGTGAC  CCGGTTCTCT
TTGACCCGCC  AGGTCCTCAA  TATAGGGCCC  CGCATCCCA   TTGGGCCTAA  TCCCGTGATC
ACTGGCCAAC  TACCCCCCTC  CCGACCCGTG  CAGATCAGGC  TCCCAGGCC   TCCTCAGACT
CCTCCTACAG  GCGCAGCCTC  TATGGTCCCT  GGGACTGCCC  CACCGTCTCA  ACAACCTGGG
```

```
ACGGGAGACA GGCTGCTAAA GCTGGTAGAT GGAGCATACC AAGCACTCAA CCTCACCAGT

CCTGACAAAA CCCAAGAGTG CTGGTTGTGT CTGGTATCGG GACCCCCTA  CTACGAAGGG

GTTGCCGTCC TAGGTACTTA CTCCAACCAT ACCTCTGCCC CAGCTAACTG CTCCGCGGCC

TCCCAACACA AGCTGACCCT GTCCGAAGTA ACCGGACAGG GACTCTGCGT AGGAGCAGTT

CCCAAAACCC ATCAGGCCCT GTGTAATACC ACCCAAAAGA CGAACGGCGG GTCCTACTAT

CTGGCTGCTC CGCCGGGAC  CATTTGGGCT TGCAACACCG GCTCACTCC  CTGCCTATCT

ACTACTGTAC TCAATCTAAC CACAGATTAT TGTGTATTAG TTGAACTCTG GCCCAGAGTA

ATTTACCACT CCCCCGATTA TATGTATGGT CAGCTTGAAC AGCGTACCAA ATATAAAAGA

GAGCCAGTAT CATTGACCCT GGCCCTTCTA CTAGGAGGAT TAACCATGGG AGGGATTGCA

GCTGGAATAG GGACGGGGAC CACTGCCTTA ATTAAACGC  AGCAGTTTGA GCAGCTTCAT

GCCGCTATCC AGACAGACCT CAACGAAGTC GAAAAGTCAA TTACCAACCT AGAAAAGTCA

CTGACCTCGT TGTCTGAAGT AGTCCTACAG AACCGCAGAG GCCTAGATTT GCTATTCCTA

AAGGAGGGAG GTCTCTGCGC AGCCCTAAAA GAAGAATGTT GTTTTATGC  AGACCACACG

GGGCTAGTGA GAGACAGCAT GGCCAAATTA AGAGAAAGGC TTAATCAGAG ACAAAAACTA

TTTGAGACAG GCCAAGGATG GTTCGAAGGG CTGTTTAATA GATCCCCTG  GTTACCACC

TTAATCTCCA CCATCATGGG ACCTCTAATA GTACTCTTAC TGATCTTACT CTTTGGACCT

TGCATTCTCA ATCGATTAGT CCAATTGTT  AAAGACAGGA TATCAGTGGT CCAGGCTCTA

GTTTTGACTC AACAATATCA CCAGCTGAAG CCTATAGAGT ACGAGCCATA G
```

(2) INFORMATION FOR SEQ ID NO: 9:

(i) SEQUENCE CHARACTERISTICS:
(A) LENGTH: 1965 bases
(B) TYPE: nucleic acid
(C) STRANDEDNESS: single
(D) TOPOLOGY: linear (ii) MOLECULE TYPE: genomic DNA (xi) SEQUENCE DESCRIPTION: SEQ ID NO: 9:

```
ATGGCGCGTT CAACGCTCTC AAAACCCCCT CAAGATAAGA TTAACCCGTG GAAGCCCTTA

ATAGTCATGG GAGTCCTGTT AGGAGTAGGG ATGGCAGAGA GCCCCCATCA GGTCTTTAAT

GTAACCTGGA GAGTCACCAA CCTGATGACT GGGCGTACCG CCAATGCCAC CTCCCTCCTG

GGAACTGTAC AAGATGCCTT CCCAAAATTA TATTTTGATC TATGTGATCT GGTCGGAGAC

GAGTGGGACC CTTCAGACCA GGAACCGTAT GTCGGGTATG CTGCAAGTA  CCCCGCAGGG

AGACAGCGGA CCCGGACTTT TGACTTTTAC GTGTGCCCTG GCATACCGT  AAAGTCGGGG

TGTGGGGGAC CAGGAGAGGG CTACTGTGGT AAATGGGGGT GTGAAACCAC CGGACAGGCT

TACTGGAAGC CCACATCATC GTGGGACCTA ATCTCCCTTA AGCGCGGTAA CACCCCCTGG

GACACGGGAT GCTCTAAAGT TGCCTGTGGC CCCTGCTACG ACCTCTCCAA AGTATCCAAT

TCCTTCCAAG GGGCTACTCG AGGGGGCAGA TGCAACCCTC TAGTCCTAGA ATTCACTGAT

GCAGGAAAAA AGGCTAACTG GGACGGGCCC AAATCGTGGG GACTGAGACT GTACCGGACA

GGAACAGATC CTATTACCAT GTTCTCCCTG ACCCGGCAGG TCCTTAATGT GGGACCCCGA

GTCCCCATAG GGCCCAACCC AGTATTACCC GACCAAAGAC TCCCTTCCTC ACCAATAGAG

ATTGTACCGG CTCCACAGCC ACCTAGCCCC CTCAATACCA GTTACCCCC  TTCCACTACC

AGTACACCCT CAACCTCCCC TACAAGTCCA AGTGTCCCAC AGCTACCCCC AGGAACTGGA
```

```
GATAGACTAC  TAGCTCTAGT  CAAAGGAGCC  TATCAGGCGC  TTAACCTCAC  CAATCCCGAC

AAGACCCAAG  AATGTTGGCT  GTGCTTAGTG  TCGGGACCTC  CTTATTACGA  AGGAGTAGCG

GTCGTGGGCA  CTTATACCAA  TCATTCCACC  GCTCCGGCCA  ACTGTACGGC  CACTTCCCAA

CATAAGCTTA  CCCTATCTGA  AGTGACAGGA  CAGGGCCTAT  GCATGGGAGC  AGTACCTAAA

ACTCACCAGG  CCTTATGTAA  CACCACCCAA  AGCGCCGGCT  CAGGATCCTA  CTACCTTGCA

GCACCCGCCG  GAACAATGTG  GGCTTGCAGC  ACTGGATTGA  CTCCCTGCTT  GTCCACCACG

GTGCTCAATC  TAACCACAGA  TTATTGTGTA  TTAGTTGAAC  TCTGGCCCAG  AGTAATTTAC

CACTCCCCCG  ATTATATGTA  TGGTCAGCTT  GAACAGCGTA  CCAAATATAA  AAGAGAGCCA

GTATCATTGA  CCCTGGCCCT  TCTACTAGGA  GGATTAACCA  TGGGAGGGAT  TGCAGCTGGA

ATAGGGACGG  GGACCACTGC  CTTAATTAAA  ACCCAGCAGT  TTGAGCAGCT  TCATGCCGCT

ATCCAGACAG  ACCTCAACGA  AGTCGAAAAG  TCAATTACCA  ACCTAGAAAA  GTCACTGACC

TCGTTGTCTG  AAGTAGTCCT  ACAGAACCGC  AGAGGCCTAG  ATTTGCTATT  CCTAAAGGAG

GGAGGTCTCT  GCGCAGCCCT  AAAAGAAGAA  TGTTGTTTTT  ATGCAGACCA  CACGGGGCTA

GTGAGAGACA  GCATGGCCAA  ATTAAGAGAA  AGGCTTAATC  AGAGACAAAA  ACTATTTGAG

ACAGGCCAAG  GATGGTTCGA  AGGGCTGTTT  AATAGATCCC  CCTGGTTTAC  CACCTTAATC

TCCACCATCA  TGGGACCTCT  AATAGTACTC  TTACTGATCT  TACTCTTTGG  ACCTTGCATT

CTCAATCGAT  TAGTCCAATT  TGTTAAAGAC  AGGATATCAG  TGGTCCAGGC  TCTAGTTTTG

ACTCAACAAT  ATCACCAGCT  GAAGCCTATA  GAGTACGAGC  CATAG
```

( 2 ) INFORMATION FOR SEQ ID NO: 10:

( i ) SEQUENCE CHARACTERISTICS:
    ( A ) LENGTH: 98 bases
    ( B ) TYPE: nucleic acid
    ( C ) STRANDEDNESS: single
    ( D ) TOPOLOGY: linear ( i i ) MOLECULE TYPE: genomic DNA ( i x ) FEATURE:
    ( A ) NAME/KEY: U3 region of LTR ( x i ) SEQUENCE DESCRIPTION: SEQ ID NO: 10:

```
GAACAGCTGA  ATATGGGCCA  AACAGGATAT  CTGTGGTAAG  CAGTTCCTGC  CCCGGCTCAG

AAGCAGTTCC  TGCCCCGGCT  CAGGGCCAAG  AACAGATG
```

( 2 ) INFORMATION FOR SEQ ID NO: 11:

( i ) SEQUENCE CHARACTERISTICS:
    ( A ) LENGTH: 75 bases
    ( B ) TYPE: nucleic acid
    ( C ) STRANDEDNESS: single
    ( D ) TOPOLOGY: linear ( i i ) MOLECULE TYPE: genomic DNA ( i x ) FEATURE:
    ( A ) NAME/KEY: U3 region of LTR ( x i ) SEQUENCE DESCRIPTION: SEQ ID NO: 11:

```
GAACAGCTGA  ATATGGGCCA  AACAGGATAT  CTGTGGTAAG  CAGTTCCTGC  CCCGGCTCAG      60

GGCCAAGAAC  AGATG                                                          75
```

( 2 ) INFORMATION FOR SEQ ID NO: 12:

( i ) SEQUENCE CHARACTERISTICS:

( A ) LENGTH: 613 bases
( B ) TYPE: nucleic acid
( C ) STRANDEDNESS: single
( D ) TOPOLOGY: linear ( i i ) MOLECULE TYPE: genomic DNA ( i x ) FEATURE:
( A ) NAME/KEY: viral LTR ( x i ) SEQUENCE DESCRIPTION: SEQ ID NO: 12:

```
GAAAGACCCC ACCTGTAGGT TTGGCAAGCT AGCTTAAGTA ACGCCATTTT GCAAGGCATG        60
GAAAAATACA TAACTGAGAA TAGAGAAGTT CAGATCAAGG TCAGGAACAG ATGGAACAGC       120
TGAATATGGG CCAAACAGGA TATCTGTGGT AAGCAGTTCC TGCCCCGGCT CAGAAGCAGT       180
TCCTGCCCCG GCTCAGGGCC AAGAACAGAT GGAACAGCTG AATATGGGCC AAACAGGATA       240
TCTGTGGTAA GCAGTTCCTG CCCCGGCTCA GGCCAAGAA CAGATGGTCC CCAGATGCGG        300
TCCAGCCCTC AGCAGTTTCT AGAGAACCAT CAGATGTTTC CAGGGTGCCC CAAGGACCTG       360
AAATGACCCT GTGCCTTATT TGAACTAACC AATCAGTTCG CTTCTCGCTT CTGTTCGCGC       420
GCTTCTGCTC CCCGAGCTCA ATAAAAAGC  CCACAACCCC TCACTCGGGG CGCCAGTCCT       480
CCGATTGACT GAGTCGCCCG GGTACCCGTG TATCCAATAA ACCCTCTTGC AGTTGCATCC       540
GACTTGTGGT CTCGCTGTTC CTTGGGAGGG TCTCCTCTGA GTGATTGACT ACCGTCAGCG       600
GGGGTCTTTC ATT                                                         613
```

( 2 ) INFORMATION FOR SEQ ID NO: 13:

( i ) SEQUENCE CHARACTERISTICS:
( A ) LENGTH: 8202 bases
( B ) TYPE: nucleic acid
( C ) STRANDEDNESS: single
( D ) TOPOLOGY: linear ( i i ) MOLECULE TYPE: genomic DNA ( i x ) FEATURE:
( A ) NAME/KEY: viral genome ( x i ) SEQUENCE DESCRIPTION: SEQ ID NO: 13:

```
CTAGCTTGCC AAACCTACAG GTGGGGTCTT TCATTCCCCC CTTTTTCTGG AGACTAAATA        60
AAATCTTTTA TTTTATCTAT GGCTCGTACT CTATAGGCTT CAGCTGGTGA TATTGTTGAG       120
TCAAAACTAG AGCCTGGACC ACTGATATCC TGTCTTTAAC AAATTGGACT AATCGATTGA       180
GAATGCAAGG TCCAAAGAGT AAGATCAGTA AGAGTACTAT TAGAGGTCCC ATGATGGTGG       240
AGATTAAGGT GGTAAACCAG GGGGATCTAT TAAACAGCCC TTCGAACCAT CCTTGGCCTG       300
TCTCAAATAG TTTTTGTCTC TGATTAAGCC TTTCTCTTAA TTTGGCCATG CTGTCTCTCA       360
CTAGCCCCGT GTGGTCTGCA TAAAAACAAC ATTCTTCTTT TAGGGCTGCG CAGAGACCTC       420
CCTCCTTTAG GAATAGCAAA TCTAGGCCTC TGCGGTTCTG TAGGACTACT TCAGACAACG       480
AGGTCAGTGA CTTTCTAGG  TTGGTAATTG ACTTTCGAC  TTCGTTGAGG TCTGTCTGGA       540
TAGCGGCATG AAGCTGCTCA AACTGCTGGG TTTTAATTAA GGCAGTGGTC CCCGTCCCTA       600
TTCCAGCTGC AATCCCTCCC ATGGTTAATC CTCCTAGTAG AAGGGCCAGG GTCAATGATA       660
CTGGCTCTCT TTTATATTTG GTACGCTGTT CAAGCTGACC ATACATATAA TCGGGGAGT        720
GGTAAATTAC TCTGGGCCAG AGTTCAACTA ATACACAATA ATCTGTGGTT AGATTGAGTA       780
CAGTAGTAGA TAGGCAGGGA GTGAGCCCGG TGTTGCAAGC CCAAATGGTC CCGGCGGGAG       840
CAGCCAGATA GTAGGACCCG TCGCTCGTCT TTTGGGTGGT ATTACACAGG GCCTGATGGG       900
```

| | | | | | |
|---|---|---|---|---|---|
| TTTTGGGAAC | TGCTCCTACG | CAGAGTCCCT | GTCCGGTTAC | TTCGGACAGG | GTCAGCTTGT | 960 |
| GTTGGGAGGC | CGCGGAGCAG | TTAGCTGGGG | CAGAGGTATG | GTTGGAGTAA | GTACCTAGGA | 1020 |
| CGGCAACCCC | TTCGTAGTAG | GGGGGTCCCG | ATACCAGACA | CAACCAGCAC | TCTTGGGTTT | 1080 |
| TGTCAGGACT | GGTGAGGTTG | AGTGCTTGGT | ATGCTCCATC | TACCAGGTTT | AGCAGCCTGT | 1140 |
| CTCCCGTCCC | AGGTTGTTGA | GACGGTGGGG | CAGTCCCAGG | GACCATAGAG | GCTGCGCCTG | 1200 |
| TAGGAGGAGT | CTGAGGAGGC | CTGGGGAGCC | TGATCTGCAC | GGGTCGGGAG | GGGGGTAGTT | 1260 |
| GGCCAGTGAT | CACGGGATTA | GGCCCAATGG | GGATGCGGGG | CCCTATATTG | AGGACCTGGC | 1320 |
| GGGTCAAAGA | GAACCGGGTC | ACCGGGTCGA | TCCCTGTGGA | TTGGTACAGT | CTTAGTCCCC | 1380 |
| ATACTTTGGG | GCCATCCCAG | CTGGCCTTTT | TACCCGCGTC | AGTGAATTCT | AGGACTAGGG | 1440 |
| GATTGCATCG | ACCCCCCGGT | GTGGCACCCT | GGATGCCACT | GGAGACCACT | GAGGAATCAT | 1500 |
| AACAGGGGCC | CTGATTCCGA | GGGGTGTTTC | CTCGCTTAAG | GGAAATTAGG | TCCCATGATG | 1560 |
| ATGATGGCTT | CCAGTATGCC | TGTCCAGTGG | TCTCACAGCC | CCATTTGCCA | CAGTAGCCCT | 1620 |
| CTCTCGGCCC | TCCACACCCT | GTTGGTACAG | TATGCCCGGG | GCAAACATAG | AAGTCAAATG | 1680 |
| TTCTTGCCCG | TTTTCTTCCC | CCGGGAGTGC | GACACCCAAG | TCCAGTCTCA | TCCCAATCGT | 1740 |
| CCCCTATTAA | ATCGCACAAG | TCGAAGTACA | GCATAGGAAA | GGCATCTGTC | ATTGTCCCCA | 1800 |
| GGAGGGAGGT | AGCGTTAGCT | GTTTGTCCTG | TCATTAAGTT | GGTAACTCTC | CAAGTAACAT | 1860 |
| TGAAGACCTG | GTGAGGGCTG | TCATGTTGTA | CTGATACTCC | TGCCCTTATT | AAGATCCCCA | 1920 |
| GGACTATCAG | GGGGCCCCAC | GGGTTAATCT | TATCTTTAAG | GGGTTTTGAG | AACGCTGGAC | 1980 |
| CTTCCATGTC | GGTCCTGATG | CTGTTCCGGC | CGGAGGGGTT | GTCGCCGCCT | TTACGTGAGC | 2040 |
| GGCGTGGATC | CACGCAGCGA | TGCCGTCTAC | TTTGAGAGCG | GTGGGGGTGG | TCAGCAGGAC | 2100 |
| GGTATAGGGT | CCTTTCCAAC | GAGGTTCCAA | GTTCTTAGTC | TGGTGCCGGC | GTACCCACAC | 2160 |
| GGTGTCGCCG | ACACGGAAGG | GGTGTGGTAT | CACTGGCTGG | TCTTGCTGGT | CCTGATAGGC | 2220 |
| CGCAGCCAGT | GGCTTCCAGA | CCTCTCGTTG | TACTGCTTGA | AGGGCCTGTA | AGTGAGCTTG | 2280 |
| GAGAGAGGGG | CTGTTAGTAA | CTCTGGTCAT | GTCAGGGTCA | GGGAAGTTTA | CAAGGGGCGG | 2340 |
| GGGTGCCCCA | TATAAGATCT | CATATGGGGT | GAGGCCATGG | GGGCCCGGCG | TGTTGCGGGC | 2400 |
| TCGGTACAGG | GCTAAGGGGA | GTAGGAGCAC | CCAGTCTCTA | GAGCCAGTTG | CAAGCGTTAA | 2460 |
| TTTAGTTAAA | GTCTCCTTGA | TGGTCCTATT | CATTCTTTCT | ACCTGACCTG | AGCTTTGGGG | 2520 |
| TCTGTATGCA | CAATGTAATT | TCCAATCAAT | CCCCAACAGA | TCGGCCACTG | TCTGACTCAC | 2580 |
| CTTGGAGACG | AAGGCAGGCC | CATTGTCAGT | TCCAATACC | TGCGGCATGC | CGAACCTAGG | 2640 |
| GAAGATCTCT | TCTAGCAGTT | TCTTGGTCAC | GACCTTGGCG | GTTTCTTTCT | TAGTTGGGAA | 2700 |
| AGCTTCTATC | CAGCCAGAAA | AAGTATCTAC | AAAAACTAAA | AGATACTTAT | AGCCATACAA | 2760 |
| TCCAGGTTTT | ACCTCGGTGA | AATCGATCTC | CCAGTGTGTG | CCAGGCCGAT | GCCCGCGGAC | 2820 |
| CCTAGTTCCT | TGCTTAACGG | CAGACTTGCT | GGCATTGACT | TGTGCACAAG | CTTTGCAGGT | 2880 |
| CTCAGTGATA | TTTTTGAGTG | TTCGATCCCG | GTTCAGCATG | TAGTAGGGAC | TGGGGCTTCT | 2940 |
| CTCTAGGAGA | GCCTTTGTTT | TTGAGAAGCT | GAGGTGGGTC | AATTGGTGAA | GAAAGTCTAG | 3000 |
| TAACTCAAAG | GTGAATTGAT | CAGGCATAAC | AGGCTTTCCT | TGAGTGACCC | AATATTTCTT | 3060 |
| CGCACTGTCA | TAAGTGGCTC | CTAGTTTGGT | CAAATCCTTT | GTGTCAGTTA | CTGTATAGTG | 3120 |
| AAAGTGTTCA | TGGGTATAGG | GGGTTGAGTT | TTCTATCAGA | AGTGTGGAAG | TTCCTGGAGT | 3180 |
| TTCTCTAGTG | GCTACTTCTC | GGGCCGCTTG | GTCGGCCATC | CGGTTGCCCC | TGGCCTCTGC | 3240 |
| GCTGTTTCCT | TTTTGATGTC | CCGGGCAATG | AATTATGCTA | AGTCTTTTGG | GCAAGAAGAG | 3300 |

| | | | | | |
|---|---|---|---|---|---|
|AGCCTTTAGT|AGGGCTAAGA|TCTCGTCCTT|GTTCTTGATC|TCTTTTCCTT|CTGATGTGAG 3360|
|CAACCCGCGC|CTTCTGTATA|TTTCTCCATG|AATATGGGCG|GTGGCAAAAG|CGTAACGGCT 3420|
|ATCAGTATAA|ACATTTAGCT|TCTTACCTTC|TGCCATCTTT|AGGGCTTGGG|TGAGCGCTAT 3480|
|CAGTTCAGCT|CTTTGGGCCG|ATGTCCGGC|TGGCAATGCC|CTGGCCCAGA|TTACCTCAGT 3540|
|CTCAGTGGTC|ACCGCTGCTC|CGGCCTTACG|CTGCCCTTCT|TGCAGGAAGC|TGCTCCCATC 3600|
|CGTGTACCAG|GTGTGGTCGG|CGTCTGGGAG|GGCTGGTCC|GTAAGATCTG|ATCTAGTTCC 3660|
|GTGGGCTTCA|GCCAAGATGT|CAAGGCAGTC|ATGTTGCAGC|CCCTCCTCAG|GCAGAGGGAG 3720|
|CAGCGTAGCT|GGATTTAGGG|CCACTACTGG|CCCGAACTGG|ACCCGGTCCG|TGTCCAGGAG 3780|
|CAGGGCTTGG|TAATGGGTCA|TCCGGGCATT|GGAGAGCCAG|CGATCAGGGG|GTTGCTTAAC 3840|
|TAGTGCCTCT|ACGGCATGGG|GGGCCAGAAT|GACCAACGGC|TGTCCCATAG|TGAGCTTGCC 3900|
|AGCATCTTTT|GTCAGAACTG|CAATGGCTGC|CACCATCCGT|AGGCAGGGG|GCCAGCCAGC 3960|
|TGCCACTGGG|TCTAGCTTTT|TAGACAGGTA|GGCCACCGGC|CGACGCCAAG|GTCCCAGCTT 4020|
|TTGCGTTAGG|ACGCCTTTGG|CGTAGCCCTG|CTTCTCGTCG|ACAAAGAGTT|CAAAGGGCTT 4080|
|AGTCAAATCT|GGCAACCCCA|GGGCTGGGGC|AGTTAGAAGA|GCTTGCTTGA|TTTCTTGATA 4140|
|GGCCTTTTGT|TGGTCTGGGC|CCCAATTAAA|CAGAGTCCCC|GTTTTGGTGA|GAGGGTACAA 4200|
|GGGGGCTGCC|ATTTCTGCAA|ACCCAGGGAT|CCAGAGGCGA|CAGAAGCCTG|CCGTCCCTAG 4260|
|GAACTCCCTT|AGTTGTCGAG|GGGTCTTCGG|AGTAGGCTCG|CCCATCACAG|TCTCTTTTCT 4320|
|GGCCTCAGTC|AGCCATCTCT|GACCCTCTTT|TAGAAGATAC|CCCAGATACT|TGACCTGTTT 4380|
|CTGGCAAATT|TGGGCTTTCT|TGGCCGAGGC|CCGATACCCG|AGGTTCCCTA|GGGTTTGTAA 4440|
|CAGGGCCCGA|GTACCTTGTT|GGCAGTCTAG|CTCAGAAGTG|GCGGCCAGCA|GTAAGTCATC 4500|
|CACGTACTGT|AGCAGGATCA|AGTCTGGGTG|CTGGATCCGG|AAGTCTGCTA|GGTCTCTGTG 4560|
|CAGTGCCTCA|TCAAACAGGG|TGGGACTGTT|TTTGAAACCC|TGTGGGAGTC|TGGTCCAGGT 4620|
|CAATTGTCCT|GAGATTCCCA|TCTCTGGATC|TCTCCACTCA|AAGGCGAAGA|GAGGCTGACT 4680|
|GGTGGGGTGG|AGTCTCAGGC|AGAAAAGGC|ATCCTTTAAA|TCAAGCACAG|TGTACCACTG 4740|
|GTGGGACGGT|GGGAGCCCGC|TCAAGAGGTT|GTAAGGGTTG|GGCACGGTGG|GGTGGATGTC 4800|
|TTCCACCCGC|TTGTTGACTT|CTCTCAGATC|CTGGACAGGC|CTATAATCAT|TAGTCCCTGG 4860|
|TTTCTTAACG|GGTAGCAGGG|GCGTGTTCCA|GGGGACTGG|CAGGGTACCA|GTAGGCCCTG 4920|
|GTCCAACAGT|CTCTGTATGT|GGGGCTTGAT|CCCCAGTCTG|GCTTCTTGTG|ACATGGGGTA 4980|
|TTGTTTTATG|GACACGGGGG|TAGAGGTTGC|TTTCAGAGGT|ATGATCAGAG|GAGCTTGGCG 5040|
|AACTGCCAGT|CCCATGCCCC|CGGTTTCCGC|CCAGGCCTGA|GGAAAATCAG|ACAGCCATGT 5100|
|GGACCCTAGA|GAAACATCTG|GCTCTTTTGA|GGTCTCATGT|AGCCGATACT|CATCTTCTAT 5160|
|ATTTAGGGTC|AACACTTGCA|GGGGCTGCCC|CATTGGTCCC|ATAACCTGAG|CTCCTGATCC 5220|
|CTCAAAGTGG|ATTTGGGCTT|TTAGTTTAGT|CAGCAAATCT|CTTCCTAACA|GAGGATAGGG 5280|
|ACAGTCTGGT|ACATGGAGGA|AAGAGTGGGT|GACCTTACCG|GTAGCTAGAT|GTACTTTGCG 5340|
|ATCCGTGGTC|CAGCGATACC|GCTTTCCTCC|AGTAGCCCCT|GGACCCAGG|CAGACTTATC 5400|
|ACTTAGGGGT|CCAGGATTTT|GGGTCAGCAC|GGAGTGTTGG|GCCCAGTAT|CTACCAGGAA 5460|
|GGTGACGGGT|TGCCCCCCGA|CTTTGAGGGT|TATCCTGGGT|TCAGGGGGG|GCTCCTGACC 5520|
|CTGACCTCCC|TAGTCATCTA|GGGTCAGGAG|GGAGGTCTGG|GGTCTTGGTC|CCCGAGGTCC 5580|
|TCGTGGTTTC|TTGGGACAAT|CTTTAGCCCA|GTGCCCCTTT|TCTTTGCAGT|AGGCACACTG 5640|
|GTCGCGATCG|AGTTGGGACC|TCCTTCGTTC|TCCTCCCTGT|CTATCCTGTT|TCTGTCCACT 5700|

| | | | | | |
|---|---|---|---|---|---|
| AACGACAGTG | GCCAATAGCT | TGCTCATCTC | TCTATGTCTC | CTACGATCTC | TTTCTTTCTC | 5760 |
| TTTCTGCTCA | TCCTCTGTCC | TACGGCGTTC | TTCTTTTTCC | TCTGTTTCTC | TCCTGATACG | 5820 |
| TTCCTCTCTT | TCTTCCGGGG | TTTCTCGTTT | ATTAAAGATC | TTTTCTGCCT | CTCTAACCAA | 5880 |
| ATCTCCAAGC | GTCTTGTTTT | TTAAATCTTC | TAACCTCTCT | AACTTCTCC | CAATGTCTGG | 5940 |
| GGCAGACTGC | CAAATGAAAG | ACATAGACAC | ATTAGTTTCT | TGCCCTGGGT | CCTCAGGGTC | 6000 |
| ATAAGGAGTG | TACCTGCGAT | AGGCTTCCTT | AAGTCTCTCT | AGGAAGGCCG | AGGGAGACTC | 6060 |
| ATTGGGCCCT | TGTGTTATTC | CTTTTACCTT | GGCCAAATTG | GTGGGGCTTC | TGCCCGCGTT | 6120 |
| TTGGAGACCC | GCTAGGAGCA | ACTGGCGATA | GTGGACTAGG | TGGTTCCTAC | CTGCCTGGGT | 6180 |
| GGTGTAATCC | CAGTCTGGGC | GCTCGAGGGG | AAAAGCGGCA | TCGACTTCAT | TGGGCAGTTG | 6240 |
| AGTGGGGCGC | CCATCATCGC | CCCGCACCGC | CTTTCTAGCC | TCTAAGAGCA | CCCGTTGTTT | 6300 |
| TTCTTCTCCG | GTCAGCAGAG | TCCCCAACAG | CTGCTGACAG | TCGTCCCAGG | TGGGCTGATG | 6360 |
| GGTGATGAGA | ACAGACTCGA | TCAGAGCTGT | CAGTTTACCT | GGATCTTCAG | AAAAAGAAGG | 6420 |
| GTTATTATTT | TTCCAGTTGT | AAAGGTCAGA | AGAGGAGAAC | GGCCAGTATT | GAAGCTGTCC | 6480 |
| GTTTCCTCCT | GCGCGGAGGG | GGAATGCCTG | CGAGGTAGTG | GAGTCGGCCA | CAGGGGCTC | 6540 |
| CCGTCTCCCA | CGTAGGCGAG | ATGCCATTGG | GGAGGGGTCC | GGTGCCTCTC | CCGCAGGGT | 6600 |
| CGCTTCTCCA | CCATTTCCGT | CCCTGTCGGA | AGGGGTGGT | CTTGGGTCCC | TATAAGGCGG | 6660 |
| GGGGTCTTCT | GTAAGTAGGT | CGATGAGCGG | CCCCCCACTG | TCAGAAAGAA | CTTGAGGTTT | 6720 |
| AGGTTTGGCG | CCTAGAGAAG | GAGTGAGGGC | TGGATAAAGG | GAGGAGCGAG | GCGGGTCGA | 6780 |
| ACGAGGAGGT | TCAAGGGGGA | GAGACGGGGC | GGATGGAGGA | AGAGGAGGCG | GAGGCTTAGG | 6840 |
| GTGTACAAAG | GGCTTGACCC | AGGGAGGGGG | GTCAAAAGCC | AAGGCTTCCC | AGGTCACGAT | 6900 |
| GTAGGGGACC | TGGTCTGGGT | GTCCATGCGG | GCCAGGTGAA | AAGACCTTGA | TCTTAACCTG | 6960 |
| GGTGATGAGG | TCTCGGTTAA | AGGTGCCGTC | TCGCGGCCAT | CCGATGTTAA | AGGTTGGCCA | 7020 |
| TTCTGCAGAG | CAGAAGGTAA | CCCAACGTCT | CTTCTTGACA | TCTACCGACT | GGTTGTGAGC | 7080 |
| GATCCGCTCG | ACATCTTTCC | AGTGACCTAA | GGTCAAACTT | AAGGGAGTGG | TAACAGTCTG | 7140 |
| GCCCATTTTT | TCAGACAAAT | ACAGAAACAC | AGTCAGACAG | AGACAACACA | GAACGATGCT | 7200 |
| GCAGCAGACA | AGACGCGCGG | CGCGGCTTCG | GTCCCAAACC | GAAAGCAAAA | ATTCAGACGG | 7260 |
| AGGCGGGAAC | TGTTTTAGGT | TCTCGTCTCC | TACCAGAACC | ACATATCCCT | CCTCTAAGGG | 7320 |
| GGGTGCACCA | AAGAGTCCAA | AACGATCGGG | ATTTTGGAC | TCAGGTCGGG | CCACAAAAAC | 7380 |
| GGCCCCCGAA | GTCCTGGGA | CGTCTCCCAG | GGTTGCGGCC | GGGTGTTCCG | AACTCGTCAG | 7440 |
| TTCCACCACG | GGTCCGCCAG | ATACAGAGCT | AGTTAGCTAA | CTAGTACCGA | CGCAGGCGCA | 7500 |
| TAAAATCAGT | CATAGACACT | AGACAATCGG | ACAGACACAG | ATAAGTTGCT | GGCCAGCTTA | 7560 |
| CCTCCCGGTG | GTGGGTCGGT | GGTCCCTGGG | CAGGGTCTC | CCGATCCCGG | ACGAGCCCCC | 7620 |
| AAATGAAAGA | CCCCGCTGA | CGGTAGTCAA | TCACTCAGAG | GAGACCCTCC | CAAGGAACAG | 7680 |
| CGAGACCACA | AGTCGGATGC | AACTGCAAGA | GGGTTTATTG | GATACACGGG | TACCCGGGCG | 7740 |
| ACTCAGTCAA | TCGGAGGACT | GGCGCCCCGA | GTGAGGGGTT | GTGGCTTTT | TTATTGAGCT | 7800 |
| CGGGGAGCAG | AAGCGCGCGA | ACAGAAGCGA | GAAGCGAACT | GATTGGTTAG | TTCAAATAAG | 7860 |
| GCACAGGGTC | ATTTCAGGTC | CTTGGGGCAC | CCTGGAAACA | TCTGATGGTT | CTCTAGAAAC | 7920 |
| TGCTGAGGGC | TGGACCGCAT | CTGGGGACCA | TCTGTTCTTG | GCCCTGAGCC | GGGGCAGGAA | 7980 |
| CTGCTTACCA | CAGATATCCT | GTTTGGCCCA | TATTCAGCTG | TTCCATCTGT | TCTTGGCCCT | 8040 |
| GAGCCGGGGC | AGGAACTGCT | TCTGAGCCGG | GGCAGGAACT | GCTTACCACA | GATATCCTGT | 8100 |

-continued

```
TTGGCCCATA TTCAGCTGTT CCATCTGTTC CTGACCTTGA TCTGAACTTC TCTATTCTCA      8160

GTTATGTATT TTTCCATGCC TTGCAAAATG GCGTTACTTA AG                         8202
```

( 2 ) INFORMATION FOR SEQ ID NO: 14:

( i ) SEQUENCE CHARACTERISTICS:
        ( A ) LENGTH: 51 bases
        ( B ) TYPE: nucleic acid
        ( C ) STRANDEDNESS: single
        ( D ) TOPOLOGY: linear ( i i ) MOLECULE TYPE: genomic DNA ( i x ) FEATURE:
        ( A ) NAME/KEY: multiple cloning site ( x i ) SEQUENCE DESCRIPTION: SEQ ID NO: 14:

```
AATTCGCGGC CGCTACGTAG TCGACGGATC CCTCGAGAAG CCTGGGCCCA T               51
```